US006320038B1

(12) United States Patent
Panula et al.

(10) Patent No.: US 6,320,038 B1
(45) Date of Patent: Nov. 20, 2001

(54) PROMOTER FOR NEUROPEPTIDE FF AND USE THEREOF FOR THERAPY AND DIAGNOSTICS

(76) Inventors: Pertti Aarre Juhani Panula, Finnträskinsalmi 31, FIN-01420 Jorvas; Annika Brandt, Laita inen 7 as 21, FIN-20900 Turku; Johanna Westerlund, Brahegatan 14 E 134, FIN-20100 Turku, all of (FI)

( * ) Notice: Subject to any disclaimer, the term of this patent is extended or adjusted under 35 U.S.C. 154(b) by 0 days.

(21) Appl. No.: 09/534,638

(22) Filed: Mar. 27, 2000

Related U.S. Application Data

(63) Continuation-in-part of application No. 09/365,755, filed on Aug. 3, 1999, now abandoned.

(51) Int. Cl.$^7$ .................................................. C07H 21/04
(52) U.S. Cl. .......................................... 536/24.1; 536/23.1
(58) Field of Search ................................ 536/24.1, 24.31, 536/23.1

(56) References Cited

PUBLICATIONS

Stephen J. Perry, A human gene encoding morphine modulating peptides related to NPFF and FMRFamide, Febs Letters vol. 409 (1997) 426–430.*

Bruce Alberts et al, Molecular Biology of The Cell Third Edition, pp. 420–421 (1994).*

Vilim et al, (Society for Neuroscience Abstracts, 1996, vol. 22, p. 1925).*

Gouardeères et al., "Antinociceptive effects of intrathecally administered F8F aminde and FMRFamide in the rat" European Journal of Pharmacology, 237, (1993), pp. 73–81.

R. Laguzzi et al., "Cardiovascular effects induced by the stimulation of neuropeptide FF receptors in the dorsal vagal comples: an autoradiographic and pharmacological study in the rat", Brain Research 11994, pp. 1–10, (1996).

Majane et al., "Mammalian FMRF–NH$_2$–Like Peptide in Rat Pituitary: Decrease by Osmotic Stimulus", Peptides, vol. 12, pp. 1303–1308, 1991.

Burke et al., "Physical Mapping of the Human NPFF GEne and Investigation of its Candidacy as a Disease Gene Locus" (Abstract), Society for Neuroscience, vol. 24, 1998, p. 2046.

Okladnova et al., "A Promoter–Associated Polymorphic Repeat Modulates PAX–6 Expression in Human Brain", Biochemical and Biophysical Research Communications, 248, pp. 402–405, 1998.

Kel et al., "Recognition of NFATp/AP–1 Composite Elements within Genes Induced upon the Activation of Immune Cells", J. Mol. Biol., (1999), 288, pp. 353–376.

Sarge et al., "Activation of Heat Shock Gene Transcription by Heat Shock Factor 1 Involves Oligomerization, Acquisition of DNA–Binding Activity, and Nuclear Localization and Can Occur in the Absence of Stress", Molecular and Cellular Biology, Mar. 1993, pp. 1392–1407.

Verweij et al., "Cell Type Specificity and Activation Requirements for NFAT–1 (Nuclear Factor of Activated T–cells) Transcriptional Activity Determined by a New Method Using Transgenic Mice to Assay Transcriptional Activity of an Individual Nuclear Factor", The Journal of Biological Chemistry, vol. 265, No. 26, Issue of Sep. 15, pp. 15788–15795, 1990.

Lenardo et al., "NF–$_k$B: Pleiotropic Mediator of Inducible and Tissue–Specific Gene Control", Cell, vol. 58, ppl 227–229, Jul. 28, 1989.

Vilim et al., "Gene for Pain Modulatory Neuropeptide NPFF: Induction in Spinal Cord by Noxious Stimuli", Molecular Pharmacology, 55:804–811, (1999).

Majane et al., "Origin of Neurophypophyseal Neuropeptide–FF (FLFQPQRF–NH$_2$), "Endocrinology, vol. 133, No. 4, pp. 1578–1584 (1993).

Yang et al., "Isolation, sequencing, synthesis, and pharmacological characterization of two brain neuropeptides that modulate the action of morphine", Proc. Natl. Acad. Sci., vol. 82, pp. 7757–7761, 11/1985.

Kivipelto et al., "Immunohistochemical Distribution and Partial Characterization of FLFQPQRFamidelike Peptides in the Central Nervous System of Rats", The Journal of Comparative Neurology, 286:269–287, (1989).

Allard et al., "Mechanisms Underlying the Cardiovascular Responses to Peripheral Administration of NPFF in the Rat[1,2]", The Journal of Pharmacology and Experimental Therapeutics, vol. 274, No. 1, pp. 577–583, (1995).

* cited by examiner

*Primary Examiner*—James Ketter
*Assistant Examiner*—Lisa Gansheroff
(74) *Attorney, Agent, or Firm*—Rothwell, Figg, Ernst & Manbeck

(57) ABSTRACT

The present invention relates to isolating, sequencing and cloning of the 5'-flanking region of neuropeptide FF (NPFF) promoter. The characterized neuropeptide FF (NPFF) promoter is useful in gene therapy and in DNA analyses, and in production of gene-modified animals.

26 Claims, 28 Drawing Sheets

```
-1852 TACAGAGTCTCAGGCTTAGAAAACCAGACAAGCTGGGCACTGTGACACACACTTTAATC
-1792 CAGCACTTGGGAGGCAGAGGCATCCTAATCTACATAGTAAATTCTAGACCACCCAAGGC
-1732 AAATGGTGACACCTGTTTACACACACACACACACACACACACACACACACACACACACA
-1672 ACACACACACACACACAGTGGAGACAGGAAAAGAGAGAGGTGGGGAGAGAAACCGAGAA
                                NFAT →
-1621 ACCCACAACAAAAGCAGCAGTGAAATATTTCAACTATAATGTATGACAAGCTCTACAGG
                                     ← TCF 11
-1552 AATCTTGAGACAAACCTTACAGAAAGGTTCACCCAAGCCTGGATGCATTGTATTCTAGA
      NFAT
-1492 CATCAGAAACCTGATCTAGAAGGTCTCCCTCTGCAGTAGAGCACCTGCCTACCATACAC
-1432 AGGCTCTTCATTTGGACTTGATTCCCAAGAAAGAAATTTTAAAATGCCACTTATCCGCA
                                                    ← GATA 1
-1372 ACCTAAAATGTAAGTTGGTTCCAATAAAGTACTTCCCTGTTGAGCAAAGAAGATGTGGAT
-1312 ACATGGTATTTCTCCAAATATGTGAGGGGCTTTTACATATGACTGAGAGATAACCTGAGA
                                              AP 1 →
-1252 CTCCATTGAACAAGCTACCACCTCTGGTAGAGGCCACCAAGAAGGTAAAGCCCACTCAGC
-1192 ACTCTCTGGAGATGGTAAGTTCCCCAGGACTGGAGTGGGAGGACAGCAAAGGGAATCACA
                      ← NFkappaB
-1132 GTTCACATTTTGAAAACACCGGGTCTGTGCTTTCCTACAAAATGCATCCCAAATGTTTCT
-1072 CCTAGCAAGTAATTCATTTTACTGTTCCCATATGTAAGTGAGGAAAAAAAGACTGTGAGC
                                                      NFAT →
-1012 AGCTTGCTTTGCTCATGGGGTAGAACCCCGACAGTCCTTCTTCTGTTTAGGCTAGAGACA
-952  TGGTACTCTGACACCTGGATTTGCAAGTGAGGTTAGGACTAGCTCCTTTAAAGGACCCTT
-892  CCCTGAACTGGAGTGATTGTCTGTCCCTAAAGCAGAACCCTAGTCGCCAGCTCCAGTAGT
       STAT 1
-832  ATATTAGAACCAGAACCAGGCAGAGCCCATGCTGACCAGACGGAACTGGAAAAATGTCAC
                                       ← ERE            NFAT →
-772  AATTCTGGGCCCCAAAGAACTAGGTCCTCAAGTCCTAGACAAAATGTATGGAAAGGGAAA
-712  TGGCTGGACGTGGCAGTGAAGAGTAGTGGCCACAAGGTGGCAGCAGAGTTTCAGTGTTGG
-652  AGGCCCAATCCCCAGTTCTCTTGCAAAGATGGGCCTGTCCACAAAATTTACAGGCCACCT
            ← MZF 1
-592  CTACTCAGTAAGGCTCCAAAAAGAGTCTCCTATCTCTCACTTAACTATTCACAGGTAAAT
                                              GATA 1
-532  CTTAAAGGGTAGTGAACCCACATTTAACCTGACTAGAAGCAGTGGGGATTGAAATGGGGC
                                                MZF 1
-472  TGTGCTCCTGATCACCCATTCCAGGCAGGAGTAGGGACCAAGCTGGTTCACCCTAGCCTG
      AML 1
-412  CACTTAACACTAGTTCCTTCCCATCCAGGACATAATGCCCAATTCTGACAGGAGTTTCTC
-352  CAGTGAGGAACAAGAGGTGATCAATTGAAGCTTCTCCAATCTGTTGAAGGATTGGAGGTT
                                     ← HSF 1
-292  CTTCTAAGGTTCCCCCAGGGTCTAACTCTGACAAACTGTCTGCAATTAATGATCCTTCCT
-232  GAGCTCCGGAGACAAGATTTATGCATCTAATAAAGTCTATATAACTCCAGGCTTAGGCTC
-172  GGGGGGAGGAAGCTAAGAGCAGAGAGTCCCCAGGGGAGTACGGGAGGGGGGGTCCCAGGT
      ← MZF 1          ← NFkappaB                  ← NFkappaB
-112  GGCTCTTAATAGAGCCATGCATTTCCATTCCTTGTCTAGATTTCCCCCCAGGCTGCCGGT
                     ← NFAT                           MZF 1
-52   GACCTGGGGGTAGGGACATCAGG[  ]GAAGACCGTGGGCACTCAGGAAGGCAGATGGCA
+7    GCATGGACTCCAAGTGGGCTGCTCTCCTGCTGCTGCTACTGCTCCTGCTGAATTGGGGCC
```

FIG. 1B

```
         TCTAGACAGATACCAGGTACCAATGTTAAATCATGATCTTACGTTTTGTGTCAGAACTTA
-9840    ----------+----------+----------+----------+----------+----------+
         AGATCTGTCTATGGTCCATGGTTACAATTTAGTACTAGAATGCAAAACACAGTCTTGAAT

TTTTGCATGCCATTCATGACTCTGGAGAGTTTTCTCCAAAAGGAAAGATGAGATTAATTT
-9779    ----------+----------+----------+----------+----------+----------+
         AAAACGTACGGTAAGTACTGAGACCTCTCAAAAGAGGTTTTCCTTTCTACTCTAATTAAA

TCTTTTGCATTCTTTGTAATTATGACAAAGAAGAGTCCTTTCTGTTCCTCTGTCCTATTT
-9719    ----------+----------+----------+----------+----------+----------+
         AGAAAACGTAAGAAACATTAATACTGTTTCTTCTCAGGAAAGACAAGGAGACAGGATAAA

TCTAACCACTTGCTCTCTACTGTTTGCCCTCCTTCCTGGCAGAAAGTCCCAAGGAAAGCT
-9659    ----------+----------+----------+----------+----------+----------+
         AGATTGGTGAACGAGAGATGACAAACGGGAGGAAGGACCGTCTTTCAGGGTTCCTTTCGA

CAGAGCCAACGGGTTCTCCAGCCCCAGTGATTCAGCACAGTTCCGCATCAGCCCCTAGCA
-9599    ----------+----------+----------+----------+----------+----------+
         GTCTCGGTTGCCCAAGAGGTCGGGGTCACTAAGTCGTGTCAAGGCGTAGTCGGGGATCGT

ATGGCCTTAGTGTTCGATCTGCAGCTGAAGCTGTGGCCACCTCGGTCCTCACTCAGATGG
-9539    ----------+----------+----------+----------+----------+----------+
         TACCGGAATCACAAGCTAGACGTCGACTTCGACACCGGTGGAGCCAGGAGTGAGTCTACC

CCAGCCAAAGGACAGAACTGAGCATGCCCATACAGTCACATGTGATCATGACCCCACAGT
-9479    ----------+----------+----------+----------+----------+----------+
         GGTCGGTTTCCTGTCTTGACTCGTACGGGTATGTCAGTGTACACTAGTACTGGGGTGTCA

CGCAGTCTGCGGGCAGATGATGCCTCCCATGATGGAGAGGTCCCCAGCCAGAGCTCGCCC
-9419    ----------+----------+----------+----------+----------+----------+
         GCGTCAGACGCCCGTCTACTACGGAGGGTACTACCTCTCCAGGGGTCGGTCTCGAGCGGG

GCCTGAGCCAAGAGAGAGATCAACTTAACCCCTCCTGTCTGTCTTGGAATTGGGCAGAAT
-9369    ----------+----------+----------+----------+----------+----------+
         CGGACTCGGTTCTCTCTCTAGTTGAATTGGGGAGGACAGACAGAACCTTAACCCGTCTTA

GGAGAGGGAGAAATTGTGTGTTGTGAGTATGGACAGATGTGGGCTTTTCTCTTTAGCCA
-9359    ----------+----------+----------+----------+----------+----------+
         CCTCTCCCTCTTTAACACACAACACTCATACCTGTCTACACCCCGAAAAGAGAAATCGGT

CATGATCATGTACGATTAACACCTGTACTAGGCGCTTCTGGCCCCAAAGCCACATAGATC
-9239    ----------+----------+----------+----------+----------+----------+
         GTACTAGTACATGCTAATTGTGGACATGATCCGCGAAGACCGGGGTTTCGGTGTATCTAG

ATCCCCCAAGGGTAGGGTTTCTTATGTACCTACAGCCAAAGGCCTTTCCATATGGTCTGA
-9179    ----------+----------+----------+----------+----------+----------+
         TAGGGGGTTCCCATCCCAAAGAATACATGGATGTCGGTTTCCGGAAAGGTATACCAGACT

GCAGTCATCCCTGGCCCTGATGCATGTGTGCCTGTCTCTTAACACTAACCCTTGCACTTG
-9119    ----------+----------+----------+----------+----------+----------+
         CGTCAGTAGGGACCGGGACTACGTACACACGGACAGAGAATTGTGATTGGGAACGTGAAC

TAGGTTTGGGGTTTCTCAGTGTCCCCTCCTCCCATTGACCTGTGGCTGTTACCTTCTTAT
-9059    ----------+----------+----------+----------+----------+----------+
         ATCCAAACCCCAAAGAGTCACAGGGGAGGAGGGTAACTGGACACCGACAATGGAAGAATA

TTCTTATTAGCATGCCACTTCCTGCCAGATGGAGGGAGGTGAGATTTGATGGCGTGTTAC
-8999    ----------+----------+----------+----------+----------+----------+
```

FIG. 1C-1

```
          AAGAATAATCGTACGGTGAAGGACGGTCTACCTCCCTCCACTCTAAACTACCGCACAATG
       TTGCTTGTCCCACCCCTAGCCACCACATGCACTCAGGACTTTGTCTCCCAATAGCTGCTT
-8939  ----------+----------+----------+----------+----------+----------+
       AACGAACAGGGTGGGGATCGGTGGTGTACGTGAGTCCTGAAACAGAGGGTTATCGACGAA

ATTTGTCTCTTTCCTCCTTCCTAAACTGCAGTGAAAACATTCACTTGTTGAGAATGTAAT
-8879  ----------+----------+----------+----------+----------+----------+
       TAAACAGAGAAAGGAGGAGGGATTTGACGTCACTTTTGTAAGTGAACAACTCTTACATTA

ACATTTAATGTATGAGGTAGCAGTGTTTCCCACCTCTTCCATGTGCTTTATTCCTATCTG
-8819  ----------+----------+----------+----------+----------+----------+
       TGTAAATTACATACTCCATCGTCACAAAGGGTGGAGAAGGTACACGAAATAAGGATAGAC

CTACCAAAAACAAACACAAACAAAAAAGCAAAACTCTGAGAGTTTGAATCATTTTTCAT
-8759  ----------+----------+----------+----------+----------+----------+
       GATGGTTTTTGTTTGTGTTTGTTTTTTTCGTTTTGAGACTCTCAAACTTAGTAAAAAGTA

TTCCAAATCTATTGGTACCTCATTTCGTCTCTTGACTTTCCTTAGTCTAGTGGTGGGGTC
-8699  ----------+----------+----------+----------+----------+----------+
       AAGGTTTAGATAACCATGGAGTAAAGCAGAGAACTGAAAGGAATCAGATCACCACCCCAG

TTTCCTACTTCCCCACTAGGCCTTGGGAACCTCATCTTGTGGCCTTATTGTTAGTGGCAA
-8639  ----------+----------+----------+----------+----------+----------+
       AAAGGATGAAGGGGTGATCCGGAACCCTTGGAGTAGAACACCGGAATAACAATCACCGTT

TGAAAAAGGAGAGAGCTGGAGACCTAACTGGGCTTCCCTGTCTCCTTCCCTACCCTCCAG
-8579  ----------+----------+----------+----------+----------+----------+
       ACTTTTTCCTCTCTCGACCTCTGGATTGACCCGAAGGGACAGAGGAAGGGATGGGAGGTC

TTCTAATCATCAGGGCAGACAGGAACAGTGTAATTTAAAACTTGTTCCATCAGGTTACTG
-8519  ----------+----------+----------+----------+----------+----------+
       AAGATTAGTAGTCCCGTCTGTCCTTGTCACATTAAATTTTGAACAAGGTAGTCCAATGAC

GATTAACTGATTCTTTTATGTTTTACAAGAGTTTACTGGCCAAAGTCTACATATTGTCAT
-8459  ----------+----------+----------+----------+----------+----------+
       CTAATTGACTAAGAAAATACAAAATGTTCTCAAATGACCGGTTTCAGATGTATAACAGTA

CTTTGGTCATCTGTGCTCCTGCCTCTCCACTGTGCTTCCCTGTCCACATCACTGCCTGTT
-8399  ----------+----------+----------+----------+----------+----------+
       GAAACCAGTAGACACGAGGACGGAGAGGTGACACGAAGGGACAGGTGTAGTGACGGACAA

CCACTATAACTACTTTAGCTCAGACCTCCTAGAGTTGTCAGACAGTAGCTGCTTCCATTC
-8339  ----------+----------+----------+----------+----------+----------+
       GGTGATATTGATGAAATCGAGTCTGGAGGATCTCAACAGTCTGTCATCGACGAAGGTAAG

TCTGTCCCTCCTACAGCTCTCAGCCTCCCTTCTTTTCTAAGGTATGTTTTGTACCCACCA
-8279  ----------+----------+----------+----------+----------+----------+
       AGACAGGGAGGATGTCGAGAGTCGGAGGGAAGAAAAGATTCCATACAAAACATGGGTGGT

GTGTCCAGCACTCTCTCAACAACCTTTTCATCTTCTCACCCAGTTCTTAGCCTACCCACT
-8219  ----------+----------+----------+----------+----------+----------+
       CACAGGTCGTGAGAGAGTTGTTGGAAAAGTAGAAGAGTGGGTCAAGAATCGGATGGGTGA

GGTTGTCTCTAGTCCTGAAATTTCGTTGAACTTGTCCATGGTACAGGCTCCAGGGCTCTG
-8159  ----------+----------+----------+----------+----------+----------+
       CCAACAGAGATCAGGACTTTAAAGCAACTTGAACAGGTACCATGTCCGAGGTCCCGAGAC

AAGCATCATGGTTGAGGTCATGGATGCTTTTGAATATAAGACTGAGTGGAGAGAGGAGGT
-8099  ----------+----------+----------+----------+----------+----------+
       TTCGTAGTACCAACTCCAGTACCTACGAAAACTTATATTCTGACTCACCTCTCTCCTCCA

ATACATTTTCCTATGTATAATCTCAGCAGAGCACTCAGGATATGGCCTGTCTGTGAGATT
-8039  ----------+----------+----------+----------+----------+----------+
```

FIG. 1C-2

```
          TATGTAAAAGGATACATATTAGAGTCGTCTCGTGAGTCCTATACCGGACAGACACTCTAA
       GCTGTCTGTGGCTGTTGGCTGTCCTTATTTTATGGGTTACAGAGAGAAAATACACCCCTC
-7979  ----------+---------+---------+---------+---------+---------+
       CGACAGACACCGACAACCGACAGGAATAAAATACCCAATGTCTCTCTTTTATGTGGGGAG

CTCTTCTTCATCTTCCCTTGGCTCTGAGCTATGCAGGCTCTTCCAGAGCCAGAGGCCTGT
-7919  ----------+---------+---------+---------+---------+---------+
       GAGAAGAAGTAGAAGGGAACCGAGACTCGATACGTCCGAGAAGGTCTCGGTCTCCGGACA

GGATAGATAGGTCAGCTTTAATAGCTCTTGAGTTGAGAATCCTTCCCATTGTCCTAGAAC
-7859  ----------+---------+---------+---------+---------+---------+
       CCTATCTATCCAGTCGAAATTATCGAGAACTCAACTCTTAGGAAGGGTAACAGGATCTTG

CACCTTCTGCCATCTGCTCAAGCCAAGTCCTCTTTTCTAGCTCCATCTTAAGTATGCAGA
-7799  ----------+---------+---------+---------+---------+---------+
       GTGGAAGACGGTAGACGAGTTCGGTTCAGGAGAAAAGATCGAGGTAGAATTCATACGTCT

ATAATTGCTTGCGTCTTTGTCTTCCAAAATTCACTGTCGTGGAGGAATGGAAATGTCGTG
-7739  ----------+---------+---------+---------+---------+---------+
       TATTAACGAACGCAGAAACAGAAGGTTTTAAGTGACAGCACCTCCTTACCTTTACAGCAC

TAGCTTATATGATTATTTCCTCAGAGTTTAGACTAGTGAGCCCATCCTGTGACATGTTTG
-7679  ----------+---------+---------+---------+---------+---------+
       ATCGAATATACTAATAAAGGAGTCTCAAATCTGATCACTCGGGTAGGACACTGTACAAAC

TATGTTTTATGTAAATTTCCCTCCTGCTCTTTAGAGTCAATGCTGAACAGGCCACACCCA
-7619  ----------+---------+---------+---------+---------+---------+
       ATACAAAATACATTTAAAGGGAGGACGAGAAATCTCAGTTACGACTTGTCCGGTGTGGGT

GTGAAAACTAGGAACTGGTTTTATAGTCTTCTCCCACAGGGTCTTAACAAAAACATCCCC
-7559  ----------+---------+---------+---------+---------+---------+
       CACTTTTGATCCTTGACCAAAATATCAGAAGAGGGTGTCCCAGAATTGTTTTTGTAGGGG

TGAGGTGACAAGGATAGCAAATGCCACAGCAGATGGTTGAGGGCAAGCCACCATCTCCAG
-7499  ----------+---------+---------+---------+---------+---------+
       ACTCCACTGTTCCTATCGTTTACGGTGTCGTCTACCAACTCCCGTTCGGTGGTAGAGGTC

GGGTTTCACTTGGCCTTAGAAACTCACAGCCATAGTTTGAGCTCAGGACTTCTTTAGATG
-7439  ----------+---------+---------+---------+---------+---------+
       CCCAAAGTGAACCGGAATCTTTGAGTGTCGGTATCAAACTCGAGTCCTGAAGAAATCTAC

GCTGCTTCCTAGGATTTTTTTTCCTGCTTATGAATTTTGTTTCTTTTTTTTTAATTGTC
-7379  ----------+---------+---------+---------+---------+---------+
       CGACGAAGGATCCTAAAAAAAAGGACGAATACTTAAAACAAAGAAAAAAAATTAACAG

TTGATTTCCCAGTAGCAGCCTTACACTAAAATATGACTGAGCTTATAGCTTCCAAGGGCC
-7319  ----------+---------+---------+---------+---------+---------+
       AACTAAAGGGTCATCGTCGGAATGTGATTTTATACTGACTCGAATATCGAAGGTTCCCGG

CCCCTTGGCTATTTTCTTCCTCCATCAGTCAAGTGTTTAATTCAGTGTAACCTACCAGTC
-7259  ----------+---------+---------+---------+---------+---------+
       GGGGAACCGATAAAAGAAGGAGGTAGTCAGTTCACAAATTAAGTCACATTGGATGGTCAG

TGTCCTGGTTGCATGTCTAGTATACGTGGAGGTTCTTTTTCACTTTCTTGACCCTTCATG
-7199  ----------+---------+---------+---------+---------+---------+
       ACAGGACCAACGTACAGATCATATGCACCTCCAAGAAAAGTGAAAGAACTGGGAAGTAC

TCTGCTTCTCTTGAGTCTTTGTTTTTATAGCAGGAAGTTAGTATTGGGGGCTTGAATGAT
-7139  ----------+---------+---------+---------+---------+---------+
       AGACGAAGAGAACTCAGAAACAAAAATATCGTCCTTCAATCATAACCCCCGAACTTACTA

GCAGGGCACCAACAGAACCATTGCAGGACTGAAATCCCCAGACTACCGATACCTTGGTGG
-7079  ----------+---------+---------+---------+---------+---------+
```

FIG. 1C-3

```
             CGTCCCGTGGTTGTCTTGGTAACGTCCTGACTTTAGGGGTCTGATGGCTATGGAACCACC
         TCGGTTCTCAGCTTCACTAAGAAAGCAGAACGGCTGCTTATGCTGAAGCCTCTGTGACAG
-7019    ----------+----------+----------+----------+----------+--------+
         AGCCAAGAGTCGAAGTGATTCTTTCGTCTTGCCGACGAATACGACTTCGGAGACACTGTC

TCAAGGGGGTCATCACCTACATTATTGCTGCCAGGGGTCACAGCCCTGACCTTTGCCTTC
-6959    ----------+----------+----------+----------+----------+--------+
         AGTTCCCCCAGTAGTGGATGTAATAACGACGGTCCCCAGTGTCGGGACTGGAAACGGAAG

CAGACTTAACTGAACCAGAACCAGATACCATAGAGGATAGCAATAAACCCTTCTTGACAT
-6899    ----------+----------+----------+----------+----------+--------+
         GTCTGAATTGACTTGGTCTTGGTCTATGGTATCTCCTATCGTTATTTGGGAAGAACTGTA

CTGACTATGATGTGTCATAGCGGGGTCTCTGGTCATGTCTATTTGGGGTTCAATATGCCT
-6839    ----------+----------+----------+----------+----------+--------+
         GACTGATACTACACAGTATCGCCCCAGAGACCAGTACAGATAAACCCCAAGTTATACGGA

CTTGTATTTGAATGTCAACTCCTGTCCCTAGGTATAGGAAATTTTGTGATATAATTTCAT
-6779    ----------+----------+----------+----------+----------+--------+
         GAACATAAACTTACAGTTGAGGACAGGGATCCATATCCTTTAAAACACTATATTAAAGTA

TAAATAGTTTGACTAATTCCTTTTTAATTTATCTCAGGTCCTCCTTCTCCCCAGTGGCTT
-6719    ----------+----------+----------+----------+----------+--------+
         ATTTATCAAACTGATTAAGGAAAAATTAAATAGAGTCCAGGAGGAAGAGGGGTCACCGAA

CTGAGGTTTGTTTGGTCTTTTAAGTATATTCCAAGCTTCTTGAAAATACTGGTAATATCT
-6659    ----------+----------+----------+----------+----------+--------+
         GACTCCAAACAAACCAGAAAATTCATATAAGGTTCGAAGAACTTTTATGACCATTATAGA

ATCTCTCTCTTTCTCTCTCTCTCTCTGTCTCTGTGTGTGTGTGTGTCTGTCTGTCTGT
-6599    ----------+----------+----------+----------+----------+--------+
         TAGAGAGAGAAAGAGAGAGAGAGAGAGACAGAGACACACACACACACAGACAGACAGACA

CTGTCTGTCTGTCTGTGTGTGTCTGAGTATATGATTGTTCCAACTTTGTGCTCCACTGCA
-6539    ----------+----------+----------+----------+----------+--------+
         GACAGACAGACAGACACACACAGACTCATATACTAACAAGGTTGAAACACGAGGTGACGT
```

FIG. 1C-4

```
       GAACTGCATGATCTTAATCTCTTGGGGACACTTTCTAGTGAGGGTTTTCACTTTCATGTT
-6479  ------------+----------+----------+----------+----------+----------+
       CTTGACGTACTAGAATTAGAGAACCCCTGTGAAAGATCACTCCCAAAAGTGAAAGTACAA

TCTTTCATGTTAATTTCTATCTTGTTCCTTTTCCATGTTTGAATGCCCTCATCAAAATCT
-6419  ------------+----------+----------+----------+----------+----------+
       AGAAAGTACAATTAAAGATAGAACAAGGAAAAGGTACAAACTTACGGGAGTAGTTTTAGA

CCCTCCATATATCTGACTTTCTCCTCCAACTTACCCACTGTTTTGTTCATTTTGGAGGTT
-6359  ------------+----------+----------+----------+----------+----------+
       GGGAGGTATATAGACTGAAAGAGGAGGTTGAATGGGTGACAAAACAAGTAAAACCTCCAA

TTGTATACAGTTCCTAGTTCATGCATTTGTATCTGAGACTTCTACATCAACTCTGAACTC
-6299  ------------+----------+----------+----------+----------+----------+
       AACATATGTCAAGGATCAAGTACGTAAACATAGACTCTGAAGATGTAGTTGAGACTTGAG

TTTCTCAGACTTCTCAGTACTTTTGGTTTTCATTAAGGAGAGGTTTGTAGTATGCCCTGG
-6239  ------------+----------+----------+----------+----------+----------+
       AAAGAGTCTGAAGAGTCATGAAAACCAAAAGTAATTCCTCTCCAAACATCATACGGGACC

TCTGCTGTTGTCTCATGTTCCTTGTGTTTCTCTGTGGAATTTTGTACATCAGTCAGGATG
-6179  ------------+----------+----------+----------+----------+----------+
       AGACGACAACAGAGTACAAGGAACACAAAGAGACACCTTAAAACATGTAGTCAGTCCTAC

GCTATGTCCTCCAGTTTTAACTCATCTTTTCCCAACTCTGTTTTGTTTCATGTAACTAAG
-6119  ------------+----------+----------+----------+----------+----------+
       CGATACAGGAGGTCAAAATTGAGTAGAAAAGGGTTGAGACAAAACAAAGTACATTGATTC

CCCTTCTTCAGAGGTCTGTCAGAAAGGCGCTGAGAGTGTGATGTCTCAGGCCCAGGTGTG
-6059  ------------+----------+----------+----------+----------+----------+
       GGGAAGAAGTCTCCAGACAGTCTTTCCGCGACTCTCACACTACAGAGTCCGGGTCCACAC

GTCAGAGGCCTGGTCTGTGCTCTTGCCACCCACTCCATATAACACAGAGTGTTCAGAGTC
-5999  ------------+----------+----------+----------+----------+----------+
       CAGTCTCCGGACCAGACACGAGAACGGTGGGTGAGGTATATTGTGTCTCACAAGTCTCAG

TCAAAGGTGAGAAGCCGCCCAACACGCAGGGAGAGCTGGGAAGGACACGGGCCCCTTCAT
-5939  ------------+----------+----------+----------+----------+----------+
       AGTTTCCACTCTTCGGCGGGTTGTGCGTCCCTCTCGACCCTTCCTGTGCCCGGGGAAGTA

TCACTTTCACTCCCTTCCTGTTGGCTGAGATGCCAGATCTGCCTGCTTCCTTCCTCCACT
-5879  ------------+----------+----------+----------+----------+----------+
       AGTGAAAGTGAGGGAAGGACAACCGACTCTACGGTCTAGACGGACGAAGGAAGGAGGTGA

CCTTCCCATGGCTGTAAGCACCAGACCACATACTTAAGGGAGCTGTGCTGGTGAACCTTG
-5819  ------------+----------+----------+----------+----------+----------+
       GGAAGGGTACCGACATTCGTGGTCTGGTGTATGAATTCCCTCGACACGACCACTTGGAAC

CCTTGCTGCCTGCCTTCCCTCTCCCATTCTGTAGCTCTTGACTCCTTCCTTGATTCACCT
-5759  ------------+----------+----------+----------+----------+----------+
       GGAACGACGGACGGAAGGGAGAGGGTAAGACATCGAGAACTGAGGAAGGAACTAAGTGGA

CTTCCGTCTCCTCAGGGACCCGCCCTCCAGCACCATCATCCTGAGAGATATAACTGTACT
-5699  ------------+----------+----------+----------+----------+----------+
       GAAGGCAGAGGAGTCCCTGGGCGGGAGGTCGTGGTAGTAGGACTCTCTATATTGACATGA

TTGTACAGCCTGAACCGCCAAAAAGACACACATGCAATTCTTCCTCTGGCTTCTGAGAGG
-5639  ------------+----------+----------+----------+----------+----------+
       AACATGTCGGACTTGGCGGTTTTTCTGTGTGTACGTTAAGAAGGAGACCGAAGACTCTCC

CTCCTTAAAGGTGCTAACTGCTCAGCTCACTCTCCCCGGCGTGTCCCCATCCTCAGAACA
-5579  ------------+----------+----------+----------+----------+----------+
       GAGGAATTTCCACGATTGACGAGTCGAGTGAGAGGGGCCGCACAGGGGTAGGAGTCTTGT
```

FIG. 1C-5

```
        CATTTCCATTATCTATTGTACCCACCAAAAAGAAATATGTACTTCTTATGAAAAGAAAAC
-5519   ----------+----------+----------+----------+----------+----------+
        GTAAAGGTAATAGATAACATGGGTGGTTTTTCTTTATACATGAAGAATACTTTCTTTTTG

CCTAGTCTGTTCAGATGTGTCTCACAGCTGTGTGACACGTGCCTTCGTTGCTATGCTTTC
-5459   ----------+----------+----------+----------+----------+----------+
        GGATCAGACAAGTCTACACAGAGTGTCGACACACTGTGCACGGAAGCAACGATACGAAAG

TCCTTTCTTTAGCCATGTTTGACCAGGGTGGGAGGGTGGATCCTAAAGCCTATCAAAAGA
-5399   ----------+----------+----------+----------+----------+----------+
        AGGAAAGAAATCGGTACAAACTGGTCCCACCCTCCCACCTAGGATTTCGGATAGTTTTCT

CCCTACCCCACTCCAGTCCAGCTAGACATTCTTCTTACAAATTCTGTTTCTGTCTGTATA
-5339   ----------+----------+----------+----------+----------+----------+
        GGGATGGGGTGAGGTCAGGTCGATCTGTAAGAAGAATGTTTAAGACAAAGACAGACATAT

TGTGCATATGCATAGACAAATCCCCCTATTCCACCAGCCTGGTGATCCATAGGAATGAGC
-5279   ----------+----------+----------+----------+----------+----------+
        ACACGTATACGTATCTGTTTAGGGGGATAAGGTGGTCGGACCACTAGGTATCCTTACTCG

AGTGCCTGCTGGCCACATTCCCACCGTTTGCACTGTTACTTTGAGGTAAAATCCTACCCT
-5219   ----------+----------+----------+----------+----------+----------+
        TCACGGACGACCGGTGTAAGGGTGGCAAACGTGACAATGAAACTCCATTTTAGGATGGGA

AGAATGAACAAAGGCTGGTGAAAGTAGGGCAGATTAAGGCAGCTTATGTTCTTGTAAATG
-5159   ----------+----------+----------+----------+----------+----------+
        TCTTACTTGTTTCCGACCACTTTCATCCCGTCTAATTCCGTCGAATACAAGAACATTTAC

CAAGTTTCTATTTCAGCTAGTAGGTGTTTTCTTTTTCTGTTTTGTTTTTTAATGTAGAGC
-5099   ----------+----------+----------+----------+----------+----------+
        GTTCAAAGATAAAGTCGATCATCCACAAAAGAAAAAGACAAAACAAAAAATTACATCTCG

TGGTAGGCTATAAGCCAGCAATTGTGAGTAAGGCTTTAGCTATTAGTGGCTGTGAGCACT
-5039   ----------+----------+----------+----------+----------+----------+
        ACCATCCGATATTCGGTCGTTAACACTCATTCCGAAATCGATAATCACCGACACTCGTGA

AGTTTCATTGACTTTACCTTAGGGCAGTGGTTCTCAGAACATGGTCCAAGAACAACATCA
-4979   ----------+----------+----------+----------+----------+----------+
        TCAAAGTAACTGAAATGGAATCCCGTCACCAAGAGTCTTGTACCAGGTTCTTGTTGTAGT

GCAGCACCATCACCTGAAGAGCTTGCTAGAAATGTACACTCTGGGCCATCCCAACCTCCT
-4919   ----------+----------+----------+----------+----------+----------+
        CGTCGTGGTAGTGGACTTCTCGAACGATCTTTACATGTGAGACCCGGTAGGGTTGGAGGA

GAGTTGGCCACTCTGAAGGTGAGCTTTAACTAACAGTCTCTGCTGCTAGTTCACACTAAT
-4859   ----------+----------+----------+----------+----------+----------+
        CTCAACCGGTGAGACTTCCACTCGAAATTGATTGTCAGAGACGACGATCAAGTGTGATTA

GCATGACAGTCCCTAGCGGACAGGCTGGGAGCATCTTAGCTCTGGGATGACAACGATTAC
-4799   ----------+----------+----------+----------+----------+----------+
        CGTACTGTCAGGGATCGCCTGTCCGACCCTCGTAGAATCGAGACCCTACTGTTGCTAATG

TTTAAATGTCTTCTCTGCCTTAGAATTGATATTTTATTTCCCCCAGTCCTTCCTTCCTC
-4739   ----------+----------+----------+----------+----------+----------+
        AAATTTACAGAAGAGACGGAATCTTAACTATAAAAATAAAGGGGGTCAGGAAGGAAGGAG

TTCCATTAAAACAGCCACCACCACATTACTCATCTCAAATTCTAGGTTGGTCTTCCTTCT
-4679   ----------+----------+----------+----------+----------+----------+
        AAGGTAATTTTGTCGGTGGTGGTGTAATGAGTAGAGTTTAAGATCCAACCAGAAGGAAGA

AGTCTTAGCTCTAAAACTCTTGCCTGCATTGGTCTGGACTCATATTTCCTTGCAGGCTAC
-4619   ----------+----------+----------+----------+----------+----------+
        TCAGAATCGAGATTTTGAGAACGGACGTAACCAGACCTGAGTATAAAGGAACGTCCGATG
```

FIG. 1C-6

```
        TAGTTCTGCATTCTTGGTGACTTTAGCCAGCAGGAAGGCCAGGAGTGGTGGTGGCATATG
-4559   ----------+----------+----------+----------+----------+----------+
        ATCAAGACGTAAGAACCACTGAAATCGGTCGTCCTTCCGGTCCTCACCACCACCGTATAC

CCTTTGATCCCAGCACTTTTGAGGGAAGCAGAGGCAGGCAGATCTCTTTGTGTTCAAGAC
-4499   ----------+----------+----------+----------+----------+----------+
        GGAAACTAGGGTCGTGAAAACTCCCTTCGTCTCCGTCCGTCTAGAGAAACACAAGTTCTG

CAGTCTGGTCTACATAGGGAGTTCAAAGCCAATCATAGCTATGCAGTGAGACCCTGTCTC
-4439   ----------+----------+----------+----------+----------+----------+
        GTCAGACCAGATGTATCCCTCAAGTTTCGGTTAGTATCGATACGTCACTCTGGGACAGAG

AAAACAAACAAACAAAATCAGCAGGAGCCTTAGTTGTCCATTTCTTCCCTGTGCACACAC
-4379   ----------+----------+----------+----------+----------+----------+
        TTTTGTTTGTTTGTTTTAGTCGTCCTCGGAATCAACAGGTAAAGAAGGGACACGTGTGTG

CACATCTCTTACAGGAAGATTAGCCTCCACCCCCACAGTGGAGCCTCCTACATCCTGATA
-4319   ----------+----------+----------+----------+----------+----------+
        GTGTAGAGAATGTCCTTCTAATCGGAGGTGGGGGTGTCACCTCGGAGGATGTAGGACTAT

GAGTATATGTTGAGAAGCCATGTGTATCTATGAATATAGCTCTGTTCTATATCCTTTTGA
-4259   ----------+----------+----------+----------+----------+----------+
        CTCATATACAACTCTTCGGTACACATAGATACTTATATCGAGACAAGATATAGGAAAACT
```

FIG. 1C-7

```
       CATGTAGCAATACCTCTCCATCCTCAAGGAACTCAACCCAGTCTGGGTCTCCCCAGGCTC
-4199  ----------+----------+----------+----------+----------+----------+
       GTACATCGTTATGGAGAGGTAGGAGTTCCTTGAGTTGGGTCAGACCCAGAGGGGTCCGAG

CAGTGGTAGACTCTGACAGGTGGGAGGATACAGTGCTCTGGGCTGTTTTGTTACAAAAGT
-4139  ----------+----------+----------+----------+----------+----------+
       GTCACCATCTGAGACTGTCCACCCTCCTATGTCACGAGACCCGACAAAACAATGTTTTCA

GTCTTCTGTCCTTTCCCTCCTCCCAATTCAGCATGACCCCTGTGAGCAGGCTCTCACAAT
-4079  ----------+----------+----------+----------+----------+----------+
       CAGAAGACAGGAAAGGGAGGAGGGTTAAGTCGTACTGGGGACACTCGTCCGAGAGTGTTA

CTCCTGGGGCAGGGCTGAGGCAGGGGCTTTCAGCTCTTCTCCATAACTATCCCTTCTTCC
-4019  ----------+----------+----------+----------+----------+----------+
       GAGGACCCCGTCCCGACTCCGTCCCCGAAAGTCGAGAAGAGGTATTGATAGGGAAGAAGG

TTCCCCCATGCCATTTAGCAGTTATCACCCAGCCTTGCCTTCTCCCTCCATCCCTTGCCC
-3959  ----------+----------+----------+----------+----------+----------+
       AAGGGGGTACGGTAAATCGTCAATAGTGGGTCGGAACGGAAGAGGGAGGTAGGGAACGGG

TGACATATACTGTGCCTTATTTATGCTGCAAATATAACATTAAACTATCAAGAGAATGAC
-3899  ----------+----------+----------+----------+----------+----------+
       ACTGTATATGACACGGAATAAATACGACGTTTATATTGTAATTTGATAGTTCTCTTACTG

TGGTATGTTTGGTGCTTCCCTACGCAGACTCATGGGGCCCATTGGTCACTCCTAGAGACT
-3839  ----------+----------+----------+----------+----------+----------+
       ACCATACAAACCACGAAGGGATGCGTCTGAGTACCCCGGGTAACCAGTGAGGATCTCTGA

CAGTAGGCATTTGTGTCTGACCATCCTCCTCCTTCCACTTCTTAGGGCAGAACTAGCAGG
-3779  ----------+----------+----------+----------+----------+----------+
       GTCATCCGTAAACACAGACTGGTAGGAGGAGGAAGGTGAAGAATCCCGTCTTGATCGTCC

CTCTCTCTGCTTTCAGTAAGTAACATGGTGTTGGAAAAGGCACAGAGTTCAGATCTTTAA
-3719  ----------+----------+----------+----------+----------+----------+
       GAGAGAGACGAAAGTCATTCATTGTACCACAACCTTTTCCGTGTCTCAGGTCTAGAAATT

ACTGCCTCAGAGCCAAGGCATCACAAAAAGACTGACCAATGGGAATACTGAACACCCTGG
-3659  ----------+----------+----------+----------+----------+----------+
       TGACGGAGTCTCGGTTCCGTAGTGTTTTTCTGACTGGTTACCCTTATGACTTGTGGGACC

CTCTTTCAGTGTTTTATGCTCACCCACTTCCAACAATTGAAAGGAAGAAAAAGTCCTACT
-3599  ----------+----------+----------+----------+----------+----------+
       GAGAAAGTCACAAAATACGAGTGGGTGAAGGTTGTTAACTTTCCTTCTTTTTCAGGATGA

CCCAAGAAAGGGGCTTGGGAGTGTACAAAGAGGTAGACAAAGTCAAGCTTTCTCCAGAGA
-3539  ----------+----------+----------+----------+----------+----------+
       GGGTTCTTTCCCCGAACCCTCACATGTTTCTCCATCTGTTTCAGTTCGAAAGAGGTCTCT

CTAGAAGGAATAGCTGAAGAGATGGCTCAGTAGTTAAGAGGAAAAACTGCTCTTGTCTCA
-3479  ----------+----------+----------+----------+----------+----------+
       GATCTTCCTTATCGACTTCTCTACCGAGTCATCAATTCTCCTTTTTGACGAGAACAGAGT

AAAGATCCGTTTGGTCCCCACACCCATGTTGGCTAGTTTACCACCACCCTTAACTCCAGC
-3419  ----------+----------+----------+----------+----------+----------+
       TTTCTAGGCAAACCAGGGGTGTGGGTACAACCGATCAAATGGTGGTGGGAATTGAGGTCG

TGCAAGGGATCTGGTGCCCTCTTTTGGCCCCCACAGGCACTGCACTCACTTGCATAACCC
-3359  ----------+----------+----------+----------+----------+----------+
       ACGTTCCCTAGACCACGGGAGAAAACCGGGGTGTCCGTGACGTGAGTGAACGTATTGGG

TTCCCCCAGCACACATATACACAATTAAAAAGTTAAAAAAAAAAAAATTAAAAAGAGAAG
-3299  ----------+----------+----------+----------+----------+----------+
       AAGGGGGTCGTGTGTATATGTGTTAATTTTTCAATTTTTTTTTTTTTAATTTTTCTCTTC
```

FIG. 1C-8

```
        AAGATTGGAAACTCGAGGCAAACTTTGTAAAAGCAGATTAAAGCTCACAGGAGAACAGGT
-3239   ----------+----------+----------+----------+----------+----------+
        TTCTAACCTTTGAGCTCCGTTTGAAACATTTTCGTCTAATTTCGAGTGTCCTCTTGTCCA

AATGATCAGGGTGAGGAAGCGGACAGGTGAGCCACTGATCCTTTCTGTGTCTGTGTCTTC
-3179   ----------+----------+----------+----------+----------+----------+
        TTACTAGTCCCACTCCTTCGCCTGTCCACTCGGTGACTAGGAAAGACACAGACACAGAAG

CACTAAAAGTGGAAACCACCAAGGAGACAGACTGAAGAACCTGACAAAAGACAGAACAGG
-3119   ----------+----------+----------+----------+----------+----------+
        GTGATTTTCACCTTTGGTGGTTCCTCTGTCTGACTTCTTGGACTGTTTTCTGTCTTGTCC

TACCTCTAAGGTTCCTTGGTAGAACAGATCTACTGGTTGGTGTCTGGTGAAGGACTTCAG
-3059   ----------+----------+----------+----------+----------+----------+
        ATGGAGATTCCAAGGAACCATCTTGTCTAGATGACCCAACCACAGACCACTTCCTGAGTC

AGCCTCCTTAGGAAATGGAAACACTTACTGGCCATCACTGTGTGGGCCCCAGCAATTAAG
-2999   ----------+----------+----------+----------+----------+----------+
        TCGGAGGAATCCTTTACCTTTGTGAATGACCGGTAGTGACACACCCGGGGTCGTTAATTC

GTACTTACTGCCAAGCCTGAAGACCTGAGCTTGATCCCTGGATACATGTGGTGGGAAGAG
-2939   ----------+----------+----------+----------+----------+----------+
        CATGAATGACGGTTCGGACTTCTGGACTCGAACTAGGGACCTATGTACACCACCCTTCTC

AACTGGCAAGGTGTTCTCTGAGCTCCACATATGCTCTGTGGGGCATGTGTCTCCTTCTCC
-2879   ----------+----------+----------+----------+----------+----------+
        TTGACCGTTCCACAAGAGACTCGAGGTGTATACGAGACACCCCGTACACAGAGGAAGAGG

CCAGGTAAATAAATGAATGAGAAAGTGGGTGGGGAGCACACAGTATGTCCAAGAAAGAGA
-2819   ----------+----------+----------+----------+----------+----------+
        GGTCCATTTATTTACTTACTCTTTCACCCACCCTCGTGTGTCATACAGGTTCTTTCTCTT

GAACATTACCAAAAGCTAAGACAGAGTCTGGAGGAAGACTGGAGAGGTGGCTCAGTGGTT
-2759   ----------+----------+----------+----------+----------+----------+
        CTTGTAATGGTTTTCGATTCTGTCTCAGACCTCCTTCTGACCTCTCCACCGAGTCACCAA

AAGAGCACTTGTGTTCTAGAGGACTTGAGTTCCGTTCCATTTAGGTGGCTCACATCTGGA
-2699   ----------+----------+----------+----------+----------+----------+
        TTCTCGTGAACACAAGATCTCCTGAACTCAAGGCAAGGTAAATCCACCGAGTGTAGACCT

ATTCTGGACTTTCGGAAGAACAGTCAGGTGCTCTTACCCACTGAGCCATCTCACCAGCCC
-2639   ----------+----------+----------+----------+----------+----------+
        TAAGACCTGAAAGCCTTCTTGTCAGTCCACGAGAATGGGTGACTCGGTAGAGTGGTCGGG

CAATATTTTTTTTTTTTTTTTGAGACAGGGTTTCTCTGTGTAGCTCTCACTGTCCTGG
-2579   ----------+----------+----------+----------+----------+----------+
        GTTATAAAAAAAAAAAAAAAAAACTCTGTCCCAAAGAGACACATCGAGAGTGACAGGACC

AACTCATTCTGTAGACCAGGCTGGCCTTGAACTCAGAGATTTGCCCTACCTCCCAAGTGC
-2519   ----------+----------+----------+----------+----------+----------+
        TTGAGTAAGACATCTGGTCCGACCGGAACTTGAGTCTCTAAACGGGATGGAGGGTTCACG

TGGGACTAAAGGCATATGTCACCACAGGCCAGCTGAGATCCTGTATTTAAATAAATAAGT
-2459   ----------+----------+----------+----------+----------+----------+
        ACCCTGATTTCCGTATACAGTGGTGTCCGGTCGACTCTAGGACATAAATTTATTTATTCA

CTGGAAGGTGATAAATAAAACTAAGTCTAGAAGATGAGAATCCTAGCACACAGGTTAGGA
-2399   ----------+----------+----------+----------+----------+----------+
        GACCTTCCACTATTTATTTTGATTCAGATCTTCTACTCTTAGGATCGTGTGTCCAATCCT

TGATTAATTTTTGTTGAGGTTAGAAGTGAACCAGCTTCTTTGTGAACTTAGTAGCTTCAG
-2339   ----------+----------+----------+----------+----------+----------+
        ACTAATTAAAAACAACTCCAATCTTCACTTGGTCGAAGAAACACTTGAATCATCGAAGTC
```

FIG. 1C-9

```
        CCCAGACTCCGGTACTGAAGCAGCAGTGCAGTGAACACAGGGTGGCTGCTGTGAGACTGC
-2279   ----------+---------+---------+---------+---------+---------+
        GGGTCTGAGGCCATGACTTCGTCGTCACGTCACTTGTGTCCCACCGACGACACTCTGACG

TGTGTACGCAACCCATCTGCTGTTCAGGACAGCTTCCTGTTCACAGGGTTAGGTTTTTTT
-2219   ----------+---------+---------+---------+---------+---------+
        ACACATGCGTTGGGTAGACGACAAGTCCTGTCGAAGGACAAGTGTCCCAATCCAAAAAAA

ATTGTTCTCTGGGTGCTGGAGATTGTGCTCAGGGGCCTCCAGCAAGTTGCCTCTTTGTTG
-2159   ----------+---------+---------+---------+---------+---------+
        TAACAAGAGACCCACGACCTCTAACACGAGTCCCCGGAGGTCGTTCAACGGAGAAACAAC

TTTTTTTGTTTGTTTGTTTTGTTTTGAGGCAGGGTTTCTCTGTGTAGCCTTGGCTGTTTT
-2099   ----------+---------+---------+---------+---------+---------+
        AAAAAAACAAACAAACAAAACAAAACTCCGTCCCAAAGAGACACATCGGAACCGACAAAA

GGAACTAGCTCTGTAGAAGAGCCTGGCCTCGACTCAAAAAGATCAGCCTGCCTCTGAAGT
-2039   ----------+---------+---------+---------+---------+---------+
        CCTTGATCGAGACATCTTCTCGGACCGGAGCTGAGTTTTTCTAGTCGGACGGAGACTTCA

CACACAGTGAATTTCGAGAGCAAAGATAAAATACGAAATTTCTGCCAGGTGTGGTGGTGC
-1979   ----------+---------+---------+---------+---------+---------+
        GTGTGTCACTTAAAGCTCTCGTTTCTATTTTATGCTTTAAAGACGGTCCACACCACCACG
```

FIG. 1C-10

```
         ACATCTGTAATCCCAGCACTTGAGAAACTAAAAACAGAGGCCAGCATATTGGGCTACATA
-1919    ------------+---------+---------+---------+---------+---------+
         TGTAGACATTAGGGTCGTGAACTCTTTGATTTTTGTCTCCGGTCGTATAACCCGATGTAT

CAGAGTCTCAGGCTTAGAAAACCAGACAAGCTGGGCACTGTGACACACACTTTAATCCCA
-1859    ------------+---------+---------+---------+---------+---------+
         GTCTCAGAGTCCGAATCTTTTGGTCTGTTCGACCCGTGACACTGTGTGTGAAATTAGGGT

GCACTTGGGAGGCAGAGGCATCCTAATCTACATAGTAAATTCTAGACCAGCCAAGGCTAA
-1799    ------------+---------+---------+---------+---------+---------+
         CGTGAACCCTCCGTCTCCGTAGGATTAGATGTATCATTTAAGATCTGGTCGGTTCCGATT

ATGGTGACACCTGTTTACACACACACACACACACACACACACACACACACACACACACAC
-1739    ------------+---------+---------+---------+---------+---------+
         TACCACTGTGGACAAATGTGTGTGTGTGTGTGTGTGTGTGTGTGTGTGTGTGTGTGTGTG

ACACACACACACACAGTGGAGACAGGAAAAGAGAGAGGTGGGGAGAGAAACCGAGAAGAC
-1679    ------------+---------+---------+---------+---------+---------+
         TGTGTGTGTGTGTGTCACCTCTGTCCTTTTCTCTCTCCACCCCTCTCTTTGGCTCTTCTG

CCACAACAAAAGCAGCAGTGAAATATTTCAACTATAATGTATGACAAGCTCTACAGGAAA
-1619    ------------+---------+---------+---------+---------+---------+
         GGTGTTGTTTTCGTCGTCACTTTATAAAGTTGATATTACATACTGTTCGAGATGTCCTTT

TCTTGAGACAAACCTTACAGAAAGGTTCACCCAAGCCTGGATGCATTGTATTCTAGAACA
-1559    ------------+---------+---------+---------+---------+---------+
         AGAACTCTGTTTGGAATGTCTTTCCAAGTGGGTTCGGACCTACGTAACATAAGATCTTGT

TCAGAAACCTGATCTAGAAGGTCTCCCTCTGCAGTAGAGCACCTGCCTACCATACACAAG
-1499    ------------+---------+---------+---------+---------+---------+
         AGTCTTTGGACTAGATCTTCCAGAGGGAGACGTCATCTCGTGGACGGATGGTATGTGTTC

GCTCTTCATTTGGACTTGATTCCCAAGAAAGAAATTTTAAAATGCCACTTATCCGCAAAC
-1439    ------------+---------+---------+---------+---------+---------+
         CGAGAAGTAAACCTGAACTAAGGGTTCTTTCTTTAAAATTTTACGGTGAATAGGCGTTTG

CTAAAATGTAAGTTGGTTCCAATAAAGTACTTCCCTGTTGAGCAAAGAAGATGTGGATAC
-1379    ------------+---------+---------+---------+---------+---------+
         GATTTTACATTCAACCAAGGTTATTTCATGAAGGGACAACTCGTTTCTTCTACACCTATG

ATGGTATTTCTCCAAATATGTGAGGGGCTTTTACATATGACTGAGAGATAACCTGAGACT
-1319    ------------+---------+---------+---------+---------+---------+
         TACCATAAAGAGGTTTATACACTCCCCGAAAATGTATACTGACTCTCTATTGGACTCTGA

CCATTGAACAAGCTAGGACCTCTGGTAGAGGCCACCAAGAAGCTAAAGCCCACTCAGCAC
-1259    ------------+---------+---------+---------+---------+---------+
         GGTAACTTGTTCGATCCTGGAGACCATCTCCGGTGGTTCTTCGATTTCGGGTGAGTCGTG

TCTCTGGAGATGGTAAGTTCCCCAGGACTGGAGTGGGAGGACAGCAAAGGGAATCACAGT
-1199    ------------+---------+---------+---------+---------+---------+
         AGAGACCTCTACCATTCAAGGGGTCCTGACCTCACCCTCCTGTCGTTTCCCTTAGTGTCA

TGACATTTTGAAAACACCGGGTCTGTGCTTTCCTACAAAATGCATCCCAAATGTTTCTCC
-1139    ------------+---------+---------+---------+---------+---------+
         ACTGTAAAACTTTTGTGGCCCAGACACGAAAGGATGTTTTACGTAGGGTTTACAAAGAGG

TAGCAAGTAATTCATTTTACTGTTCCCATATGTAAGTGAGGAAAAAAAGAGTGTGAGCAG
-1079    ------------+---------+---------+---------+---------+---------+
         ATCGTTCATTAAGTAAAATGACAAGGGTATACATTCACTCCTTTTTTCTCACACTCGTC

CTTGCTTTGCTCATGGGGTAGAACCCCGACAGTCCTTCTTCTGTTTAGGCTAGAGACATG
-1019    ------------+---------+---------+---------+---------+---------+
         GAACGAAACGAGTACCCCATCTTGGGGCTGTCAGGAAGAAGACAAATCCGATCTCTGTAC
```

FIG. 1C-11

```
      GTACTCTGACACCTGGATTTGCAAGTGAGGTTAGGACTAGCTCCTTTAAAGGACCCTTCC
-959  ------------+---------+---------+---------+---------+---------+
      CATGAGACTGTGGACCTAAACGTTCACTCCAATCCTGATCGAGGAAATTTCCTGGGAAGG

CTGAACTGGAGTGATTGTCTGTCCCTAAAGCAGAACCCTAGTCGCCAGCTCCAGTAGTAT
-899  ------------+---------+---------+---------+---------+---------+
      GACTTGACCTCACTAACAGACAGGGATTTCGTCTTGGGATCAGCGGTCGAGGTCATCATA

ATTAGAACCAGAACCAGGCAGAGCCCATGCTGACCAGACGGAACTGGAAAAATGTCACAA
-839  ------------+---------+---------+---------+---------+---------+
      TAATCTTGGTCTTGGTCCGTCTCGGGTACGACTGGTCTGCCTTGACCTTTTTACAGTGTT

TTCTGGGCCCCAAAGAACTAGGTCCTCAAGTCCTAGACAAAATGTATGGAAAGGGAAATG
-779  ------------+---------+---------+---------+---------+---------+
      AAGACCCGGGGTTTCTTGATCCAGGAGTTCAGGATCTGTTTTACATACCTTTCCCTTTAC

GCTGGACGTGGCAGTGAAGAGTAGTGGCCACAAGGTGGCAGCAGAGTTTCAGCTGTGGAG
-719  ------------+---------+---------+---------+---------+---------+
      CGACCTGCACCGTCACTTCTCATCACCGGTGTTCCACCGTCGTCTCAAAGTCGACACCTC

GCCCAATCCCCAGTTCTCTTGCAAAGATGGGCCTGTCCACAAAATTTACAGGCCACCTCT
-659  ------------+---------+---------+---------+---------+---------+
      CGGGTTAGGGGTCAAGAGAACGTTTCTACCCGGACAGGTGTTTTAAATGTCCGGTGGAGA

ACTCAGTAAGGCTCCAAAAAGAGTCTCCTATCTCTCACTTAACTATTCACAGGTAAATCT
-599  ------------+---------+---------+---------+---------+---------+
      TGAGTCATTCCGAGGTTTTTCTCAGAGGATAGAGAGTGAATTGATAAGTGTCCATTTAGA

TAAAGGGTAGTGAACCCACATTTAACCTGACTAGAAGCAGTGGGGATTGAAATGGGGCTG
-539  ------------+---------+---------+---------+---------+---------+
      ATTTCCCATCACTTGGGTGTAAATTGGACTGATCTTCGTCACCCCTAACTTTACCCCGAC

TGGTCCTGATCACCCATTCCAGGCAGGAGTAGGGACCAAGCTGGTTCACCCTAGCCTGCA
-479  ------------+---------+---------+---------+---------+---------+
      ACCAGGACTAGTGGGTAAGGTCCGTCCTCATCCCTGGTTCGACCAAGTTGGATCGGACGT

CTTAACACTAGTTCCTTCCCATCCAGGACATAATGCCCAATTCTGACAGGAGTTTCTCCA
-419  ------------+---------+---------+---------+---------+---------+
      GAATTGTGATCAAGGAAGGGTAGGTCCTGTATTACGGGTTAAGACTGTCCTCAAAGAGGT

GTCAGGAACAAGAGGTGATCAATTGAAGCTTCTCCAATCTGTTGAAGGATTGGAGGTTCT
-359  ------------+---------+---------+---------+---------+---------+
      CAGTCCTTGTTCTCCACTAGTTAACTTCGAAGAGGTTAGACAACTTCCTAACCTCCAAGA

TCTAAGGTTCCCCCAGGGTCTAACTCTGACAAACTGTCTGCAATTAATGATGCTTCTTGA
-299  ------------+---------+---------+---------+---------+---------+
      AGATTCCAAGGGGGTCCCAGATTGAGACTGTTTGACAGACGTTAATTACTACGAAGGACT

GCTCCGGAGACAAGATTTATGCATCTAATAAAGTCTATATAACTCCGGTCTTAGGCTGGG
-239  ------------+---------+---------+---------+---------+---------+
      CGAGGCCTCTGTTCTAAATACGTAGATTATTTCAGATATATTGAGGTCCGAATCCGACCC

GGGGAGGAAGCTAAGAGCAGAGAGTCCCCAGGGGAGTACGGGAGGGGGGTCCCAGGTGG
-179  ------------+---------+---------+---------+---------+---------+
      CCCCTCCTTCGATTCTCGTCTCTCAGGGGTCCCCTCATGCCCTCCCCCCAGGGTCCACC

CTCTTAATAGAGCCATGCATTTCCATTGCTTGTCTAGATTTCCCCCCAGGCTGCCGGTGA
-119  ------------+---------+---------+---------+---------+---------+
      GAGAATTATCTCGGTACGTAAAGGTAACGAACAGATCTAAAGGGGGGTCCGACGGCCACT

GGTGGGGGTAGGGACATCAGGTATAAGAAGACCGTGGGCACTCAGGAGGCAGATGGCAGC
-59   ------------+---------+---------+---------+---------+---------+
      CCACCCCCATCCCTGTAGTCCATATTCTTCTGGCACCCGTGAGTCCTCCGTCTACCGTCG
```

FIG. 1C-12

```
     ATGGACTCCAAGTGGGCTGCTCTGCTGCTGCTGCTACTGCTGCTGCTGAATTGGGGCCAC
  1  ------------+---------+---------+---------+---------+---------+  60
     TACCTGAGGTTCACCCGACGAGACGACGACGACGATGACGACGACGACTTAACCCCGGTG

ACTGAAGAGGCAGGGAGCTGGGGTGAAGACCAAGTCTTTGCAGTGAGTGAACATCCTGCT
 61  ------------+---------+---------+---------+---------+---------+ 120
     TGACTTCTCCGTCCCTCGACCCCACTTCTGGTTCAGAAACGTCACTCACTTGTAGGACGA

GCCCCATCCACCCAGCCGCCATCTCTCCTTCAGCTGAAACTTATGATACAGGGTTTGGTG
121  ------------+---------+---------+---------+---------+---------+ 180
     CGGGGTAGGTGGGTCGGCGGTAGAGAGGAAGTCGACTTTGAATACTATGTCCCAAACCAC

TTCCCCAGGCTGCTAAGGTCTTCAAAAAGTCTGGCTTCTAAGGGAGGGAAATGGCTTCTC
181  ------------+---------+---------+---------+---------+---------+ 240
     AAGGGGTCCGACGATTCCAGAAGTTTTTCAGACCGAAGATTCCCTCCCTTTACCGAAGAG

AGCCCACGCAAGTTTCCCCTAGAAGCCATTCTTTCCCTCCATGTCTTCAGTGTACAAGAC
241  ------------+---------+---------+---------+---------+---------+ 300
     TCGGGTGCGTTCAAAGGGGATCTTCGGTAAGAAAGGGAGGTACAGAAGTCACATGTTCTG

ACTGCCAGGTTCCTTCCCTGCCACTCTCTCATCACAGGGAGAAGATAAGGGACCCCACCC
301  ------------+---------+---------+---------+---------+---------+ 360
     TGACGGTCCAAGGAAGGGACGGTGAGAGAGTAGTGTCCCTCTTCTATTCCCTGGGGTGGG

ACCACAGTATGCCCACATTCCAGACAGGATCCAGACTCCTGGGTCCCTCTTTCGTGTTCT
361  ------------+---------+---------+---------+---------+---------+ 420
     TGGTGTCATACGGGTGTAAGGTCTGTCCTAGGTCTGAGGACCCAGGGAGAAAGCACAGGA

GCTCCAGGCCATGGACACACCTAGAAGGAGCCCAGCCTTCCTGTTTCAGCCCCAGAGGTG
421  ------------+---------+---------+---------+---------+---------+ 480
     CGAGGTCCGGTACCTGTGTGGATCTTCCTCGGGTCGGAAGGACAAAGTCGGGGTCTCCAC

AGTTCCAAAGGGAAGAGGCTGAGAAGGGTGGAGGGCAGAGGAAGATGTGAGAGAAGGTGA
481  ------------+---------+---------+---------+---------+---------+ 540
     TCAAGGTTTCCCTTCTCCGACTCTTCCCACCTCCCGTCTCCTTCTACACTCTCTTCCACT

GATGGAGGGAGTGCCAACTAAGGATGAATCTCTCCTAAGGTTTGGCAGAAGTGCATGGGG
541  ------------+---------+---------+---------+---------+---------+ 600
     CTACCTCCCTCACGGTTGATTCCTACTTAGAGAGGATTCCAAACCGTCTTCACGTACCCC

GTCCTGGAGCAAGGAACAGCTAAATCCGCAGGCCAGACAGTTCTGGAGCCTGGCCGCTCC
601  ------------+---------+---------+---------+---------+---------+ 660
     CAGGACCTCGTTCCTTGTCGATTTAGGCGTCCGGTCTGTCAAGACCTCGGACCGGCGAGG

TCAGCGCTTTGGGAAGAAGTAGCATCGTCAGCTGTGATGCCTGCATGCAAAACCACTTCC
661  ------------+---------+---------+---------+---------+---------+ 720
     AGTCGCGAAACCCTTCTTCATCGTAGCAGTCGACACTACGGACGTACGTTTTGGTGAAGG

CCATGTTCCCTGTGTGCCCCCAAATAAAAATGGTCCGGCTGGCTTCAGAATCCCTGTGTT
721  ------------+---------+---------+---------+---------+---------+ 780
     GGTACAAGGGACACACGGGGGTTTATTTTTACCAGGCCGACCGAAGTCTTAGGGACACAA

TGGACAAGACTGTCAGGGAGCAGGTGGGAGCCCAAGGGCAATAGCTGTAGCCCCCCTTCA
781  ------------+---------+---------+---------+---------+---------+ 840
     ACCTGTTCTGACAGTCCCTCGTCCACCCTCGGGTTCCCGTTATCGACATCGGGGGGAAGT

CCTCCACTCAGTCTCTAGCCATTCTGTTGTTAAGGATCCCCAAGGCTACTACTGCACCTT
841  ------------+---------+---------+---------+---------+---------+ 900
```

FIG. 1D-1

```
                GGAGGTGAGTCAGAGATCGGTAAGACAACAATTCCTAGGGGTTCCGATGATGACGTGGAA

GCCTCCTCTCGGTAACAAAAAAGAACAAGGGGTTCAAAAGGAGAACAAGCTCACCATGTT
901   ----------+----------+----------+----------+----------+----------+ 960
      CGGAGGAGAGCCATTGTTTTTTCTTGTTCCCCAAGTTTTCCTCTTGTTCGAGTGGTACAA

TATTCCTTATACCCTCATGACCCAAGGCCAGAGAGAGCAGGGTTTTGGAAGCCAAAGAGC
961   ----------+----------+----------+----------+----------+----------+ 1020
      ATAAGGAATATGGGAGTACTGGGTTCCGGTCTCTCTCGTCCCAAAACCTTCGGTTTCTCG

AGCATTTATTCAGGACTCCAATAGATTCATCCATCACCCACGGAATGAGGACAAATCCTG
1021  ----------+----------+----------+----------+----------+----------+ 1080
      TCGTAAATAAGTCCTGAGGTTATCTAAGTAGGTAGTGGGTGCCTTACTCCTGTTTAGGAC

TGCTGGCTGGGGCCCTGTGGTTCATGGCTCCTTGCTTGCCTGTGCCTTCCTCAGTCTCAA
1081  ----------+----------+----------+----------+----------+----------+ 1140
      ACGACCGACCCCGGGACACCAAGTACCGAGGAACGAACGGACACGGAAGGAGTCAGAGTT

GGCAGACAGGCTGTGTCAGAGGTAGAGATGGCACTTCTGGAGGGTACCAGAGCTAGGTGG
1141  ----------+----------+----------+----------+----------+----------+ 1200
      CCGTCTGTCCGACACAGTCTCCATCTCTACCGTGAAGACCTCCCATGGTCTCGATCCACC

ATACATGGACCCAGGGGCAGAAGGAGCAAGAAGTAAAAGATGCATATCCATCACTGCAGT
1201  ----------+----------+----------+----------+----------+----------+ 1260
      TATGTACCTGGGTCCCCGTCTTCCTCGTTCTTCATTTTCTACGTATAGGTAGTGACGTCA

GGGATGCTACTTGCTACCCGCCATGATCCTGAGGTACTGTAGGGCGCGGTGAGCAGCATC
1261  ----------+----------+----------+----------+----------+----------+ 1320
      CCCTACGATGAACGATGGGCGGTACTAGGACTCCATGACATCCCGCGCCACTCGTCGTAG

ACCTCGGGCTGCCTCCCTGGTGGTTGCAGAACCATAACACACAGTGGCTGGCTGGGTGGA
1321  ----------+----------+----------+----------+----------+----------+ 1380
      TGGAGCCCGACGGAGGGACCACCAACGTCTTGGTATTGTGTGTCACCGACCGACCCACCT

CAGTTCCACTAGGCACTGGCAGAGCCCACTCAGGCTCAGTTCCTCTGGAAACCAAGAAAG
1381  ----------+----------+----------+----------+----------+----------+ 1440
      GTCAAGGTGATCCGTGACCGTCTCGGGTGAGTCCGAGTCAAGGAGACCTTTGGTTCTTTC

AGAAGGGAGGCACTGGTGGGGAAGGGGCACCAAACAGTGTACACATCACCCATCTCCCAA
1441  ----------+----------+----------+----------+----------+----------+ 1500
      TCTTCCCTCCGTGACCACCCCTTCCCCGTGGTTTGTCACATGTGTAGTGGGTAGAGGGTT

CTCCTTCATACTTGCTTTGATCCAGTCCCCTCCATCCCCAGTCTCTAGTTGGCCATACCA
1501  ----------+----------+----------+----------+----------+----------+ 1560
      GAGGAAGTATGAACGAAACTAGGTCAGGGGAGGTAGGGGTCAGAGATCAACCGGTATGGT

ATATCCAGATAGCTGACATGGAAAGCCTGCTCCTCAGAGAGCTCACTGAGGACACTGCAG
1561  ----------+----------+----------+----------+----------+----------+ 1620
      TATAGGTCTATCGACTGTACCTTTCGGACGAGGAGTCTCTCGAGTGACTCCTGTGACGTC

CAGGCAGAGCCCAGAGCCCCTAGAGAGCCCACGGAGCAACTGCGAAGGGATAGGATCTTT
1621  ----------+----------+----------+----------+----------+----------+ 1680
      GTCCGTCTCGGGTCTCGGGGATCTCTCGGGTGCCTCGTTGACGCTTCCCTATCCTAGAAA

TCTCCCACAGAATTCCGCAAGGAATCCCAGGTGCAGCCTGGCCCACGATTCCTCAGTCCA
1681  ----------+----------+----------+----------+----------+----------+ 1740
      AGAGGGTGTCTTAAGGCGTTCCTTAGGGTCCACGTCGGACCGGGTGCTAAGGAGTCAGGT

TCCAGGCGGGAGCTCACGCCCTAATGAGATAAGAGTGAGAAAGCAGCTAAGGACTGTGGG
1741  ----------+----------+----------+----------+----------+----------+ 1800
      AGGTCCGCCCTCGAGTGCGGGATTACTCTATTCTCACTCTTTCGTCGATTCCTGACACCC

ACCCAAGAACTGGGTATTATGCTCTGACTCCTGGCAGCCTTCCTCATCCCAGGAAAAGTT
1801  ----------+----------+----------+----------+----------+----------+ 1860
```

FIG. 1D-2

```
                TGGGTTCTTGACCCATAATACGAGACTGAGGACCGTCGGAAGGAGTAGGGTCCTTTTCAA
        GCCTATAGGGGCTTTGCCCTAGGCCAGCTTTCACTAGTGACCCTACATATAGGCTGAGGG
1861    ------------+---------+---------+---------+---------+---------+ 1920
        CGGATATCCCCGAAACGGGATCCGGTCGAAAGTGATCACTGGGATGTATATCCGACTCCC

GACTTCTGGGCGCACAGGTTCAAGGAGCCCTGGGAAGGAAAGCAGGCCCATACTCACTTC
1921    ------------+---------+---------+---------+---------+---------+ 1980
        CTGAAGACCCGCGTGTCCAAGTTCCTCGGGACCCTTCCTTTCGTCCGGGTATGAGTGAAG

CAAACCACAGACCCAACCCAATTCCGTACCATGTCCTGCAGTGTGAACCACATGTCGAGC
1981    ------------+---------+---------+---------+---------+---------+ 2040
        GTTTGGTGTCTGGGTTGGGTTAAGGCATGGTACGAGACGTCACACTTGGTGTACAGCTCG

CCACACAAGCCACTTACAATGGAAAAATGATCGTCATCAGGCTCTGCCTCATTGCCATCC
2041    ------------+---------+---------+---------+---------+---------+ 2100
        GGTGTGTTCGGTGAATGTTACCTTTTTACTAGCAGTAGTCCGAGACGGAGTAACGGTAGG

CGGGCATCCAGAGGTACAAGTGTGCACTCGAAGGAGCATCTTAGCTGCTGCGTTACGCTT
2101    ------------+---------+---------+---------+---------+---------+ 2160
        GCCCGTAGGTCTCCATGTTCACACGTGAGCTTCCTCGTAGAATCGACGACGCAATGCGAA

TGCCAGCTTTTTGGAAGTGCCACTGCCTGAGGGTGGGGAAGGAATTGTTCAACTTGGGG
2161    ------------+---------+---------+---------+---------+---------+ 2220
        ACGGTCGAAAAACCTTCACGGTGACGGACTCCCACCCCCTTCCTTAACAAGTTGAACCCC

ATTCCTAACAGACCAATGCTTTCCTCTAGGGTAACTTAGACAGTCACCCAATGAGATACC
2221    ------------+---------+---------+---------+---------+---------+ 2280
        TAAGGATTGTCTGGTTACGAAAGGAGATCCCATTGAATCTGTCAGTGGGTTACTCTATGG

ACTGCAAAGAGGAGCTCAAGGCCTGATCTTTTTAACTGAGGAGTTGGTGAGCCAGATAAG
2281    ------------+---------+---------+---------+---------+---------+ 2340
        TGACGTTTCTCCTCGAGTTCCGGACTAGAAAAATTGACTCCTCAACCACTCGGTCTATTC

AGGGGGAAAGATGGGCAGGGACAAGGGAGAGACAGGAAGGCAGGAGCTGAGCAAGGACCT
2341    ------------+---------+---------+---------+---------+---------+ 2400
        TCCCCCTTTCTACCCGTCCCTGTTCCCTCTCTGTCCTTCCGTCCTCGACTCGTTCCTGGA

GCAAAGCAAAGGAAGCTGGGACAGAGCACAGCCAGGCAAAGAACCACCTTGTGTTTGGGG
2401    ------------+---------+---------+---------+---------+---------+ 2460
        CGTTTCGTTTCCTTCGACCCTGTCTCGTGTCGGTCCGTTTCTTGGTGGAACACAAACCCC

TTACAGTGTGGCAAAGAGAGAAGGTGAGTGAACCCCCTTTTCCCCAGTTACCAATCTCAA
2461    ------------+---------+---------+---------+---------+---------+ 2520
        AATGTCACACCGTTTCTCTCTTCCACTCACTTGGGGGAAAAGGGGTCAATGGTTAGAGTT

TGAAACGCTCCACCCGGCAAGTCATGGTGAACTCTTTGCGGTGAGCAGGCCCAGACTCTT
2521    ------------+---------+---------+---------+---------+---------+ 2580
        ACTTTGCGAGGTGGGCCGTTCAGTACCACTTGAGAAACGCCACTCGTCCGGGTCTGAGAA

GGGTCACCATGTACTCTGGCAAACGCCAGCCTTTTTGCACCACCAGCTCCTTGAAAGAAA
2581    ------------+---------+---------+---------+---------+---------+ 2640
        CCCAGTGGTACATGAGACCGTTTGCGGTCGGAAAAACGTGGTGGTCGAGGAACTTTCTTT

ACCATAAGAGAGTCCAAGGCTTAGTGAGGAAAGGGTCCTTAGCCAATGGCCTTCTACCAA
2641    ------------+---------+---------+---------+---------+---------+ 2700
        TGGTATTCTCTCAGGTTCCGAATCACTCCTTTCCCAGGAATCGGTTACCGGAAGATGGTT

GAGCCTCCACCTTTGAGTGAGAAGGAGGACCACCCTACCCACAAGTGCACACGCCCCTGC
2701    ------------+---------+---------+---------+---------+---------+ 2760
        CTCGGAGGTGGAAACTCACTCTTCCTCCTGGTGGGATGGGTGTTCACGTGTGCGGGGACG

CTCAGCCCTACTTCAGAGAAGATAGCACACATGACAATGAAGACCAGGCACACCTGCAGA
2761    ------------+---------+---------+---------+---------+---------+ 2820
```

FIG. 1D-3

```
                GAGTCGGGATGAAGTCTCTTCTATCGTGTGTACTGTTACTTCTGCTCCGTGTGGACGTCT
       GCACCGACGGGGTTGCACTCAGACTGCTGAGGAGAGACAGGGGGCTGCATCTCCATGGGA
2821   ------------+---------+---------+---------+---------+---------+ 2880
       CGTGGCTGCCCCAACGTGAGTCTGACGACTCCTCTCTGTCCCCCGACGTAGAGGTACCCT
       GGGCTCCTAAAGAAAAAAGGGCCCAGGCCAGTGCTGAGGAAAATGCAGAGGTTCCTCCTG
2881   ------------+---------+---------+---------+---------+---------+ 2940
       CCCGAGGATTTCTTTTTTCCCGGGTCCGGTCACGACTCCTTTTACGTCTCCAAGGAGGAC
       TCCTGGTCATGGATCAAGTGCCAGCCACTACCACCTCCCAATTCCTCACCAGGCAGGCAG
2941   ------------+---------+---------+---------+---------+---------+ 3000
       AGGACCAGTACCTAGTTCACGGTCGGTGATGGTGGAGGGTTAAGGAGTGGTCCGTCCGTC
       CTATCTGTCCAAACATCTAGCCTTTCTCCTCCCTCCCCACACCCCACCAAGTGAGGCTCT
3001   ------------+---------+---------+---------+---------+---------+ 3060
       GATAGACAGGTTTGTAGATCGGAAAGAGGAGGGAGGGGTGTGGGGTGGTTCACTCCGAGA
       GCTACTTCCCAGGAGCACTTAGATGTGGAAATCCTTCAGCAATGTCCCTGTGATGGAGGT
3061   ------------+---------+---------+---------+---------+---------+ 3120
       CGATGAAGGGTCCTCGTGAATCTACACCTTTAGGAAGTCGTTACAGGGACACTACCTCCA
       AAAGGAGCTGTACACACAGTCCTGGAAGTACCTTTTGGGTCTCAAACATGGAGCCTCTAA
3121   ------------+---------+---------+---------+---------+---------+ 3180
       TTTCCTCGACATGTGTGTCAGGACCTTCATGGAAAACCCAGAGTTTGTACCTCGGAGATT
       GATGTTTAAACAATCTAACATTCATTGCTTGGCTATTTAATCATCATAAATTACCTCCTA
3181   ------------+---------+---------+---------+---------+---------+ 3240
       CTACAAATTTGTTAGATTGTAAGTAACGAACCGATAAATTAGTAGTATTTAATGGAGGAT
       GCTCAGGCTTACCAACCAGCTGGTGCAAATTTTTCAATTACACCAGTCTGTCTTTACTCT
3241   ------------+---------+---------+---------+---------+---------+ 3300
       CGAGTCCGAATGGTTGGTCGACCACGTTTAAAAAGTTAATGTGGTCAGACAGAAATGAGA
       CAGGCTTCCTCATCCTGACCTGCCTGAGTCCAAGAGCTATGAGACTAGAAGCCAAGACCC
3301   ------------+---------+---------+---------+---------+---------+ 3360
       GTCCGAAGGAGTAGGACTGGACGGACTCAGGTTCTCGATACTCTGATCTTCGGTTCTGGG
```

FIG. 1D-4

```
       CCTCCTTCCTCCAAGACGTCAGGGGACTCAAGATACCTGGTTAGTACAGCAGATGGAACA
3361   ------------+---------+---------+---------+---------+---------+ 3420
       GGAGGAAGGAGGTTCTGCAGTCCCCTGAGTTCTATGGACCAATCATGTCGTCTACCTTGT

GGGGCAGCAGCTTCTGCAGCAACGACAGGAGTGTCCTCAGGCGGTGAAGAGTCTAGGAGA
3421   ------------+---------+---------+---------+---------+---------+ 3480
       CCCCGTCGTCGAAGACGTCGTTGCTGTCCTCACAGGAGTCCGCCACTTCTCAGATCCTCT

GAAAAAGAACTTCCCGAGGGGAAGAAGGTCTTGGATTCACACCCATGTAGAAGGGAATGA
3481   ------------+---------+---------+---------+---------+---------+ 3540
       CTTTTTCTTGAAGGGCTCCCCTTCTTCCAGAACCTAAGTGTGGGTACATCTTCCCTTACT

GGGTGTGAGGTCCTTCTGACCTTTCCATCCCCTGAGAACTCCTTCCCCCCGATGCAGACT
3541   ------------+---------+---------+---------+---------+---------+ 3600
       CCCACACTCCAGGAAGACTGGAAAGGTAGGGGACTCTTGAGGAAGGGGGGCTACGTCTGA

CGGAGAGCCTCAGCAACAGCTCTTCCTCCTGGGATCCTCTGCTGACCCCACACTGGCTCA
3601   ------------+---------+---------+---------+---------+---------+ 3660
       GCCTCTCGGAGTCGTTGTCGAGAAGGAGGACCCTAGGAGACGACTGGGGTGTGACCGAGT

GAAGCACTGAGGTTAGGGTGGGGGCTCAGAAAAGAGTCTCTTTCTACCCAACAAGCTGCA
3661   ------------+---------+---------+---------+---------+---------+ 3720
       CTTCGTGACTCCAATCCCACCCCCGAGTCTTTTCTCAGAGAAAGATGGGTTGTTCGACGT

ACCTGAATGTGGAAGAGGGAAAGCCATCTTGCTAGAAAGAGGGGGCATGCCAGGACCAAC
3721   ------------+---------+---------+---------+---------+---------+ 3780
       TGGACTTACACCTTCTCCCTTTCGGTAGAACGATCTTTCTCCCCCGTACGGTCCTGGTTG

TTTATCAGTCTTTGCCTCCACCCCCTATGCCCTTTTCTCATGCCCCAGAGCAGCCACCAC
3781   ------------+---------+---------+---------+---------+---------+ 3840
       AAATAGTCAGAAACGGAGGTGGGGGATACGGGAAAAGAGTACGGGGTCTCGTCGGTGGTG

CCATCAAAGGGGGCTGGCTATTACTCTGAGGCACTCTAGAAACACCCTGTTCAGCTTCAG
3841   ------------+---------+---------+---------+---------+---------+ 3900
       GGTAGTTTCCCCCGACCGATAATGAGACTCCGTGAGATCTTTGTGGGACAAGTCGAAGTC

AGGAAAATTCTCAGGAAGGGGCCACGAGAGGGTGGCCATGAGTCACCAGACCAGGCTTAGG
3901   ------------+---------+---------+---------+---------+---------+ 3960
       TCCTTTAAGAGTCCTTCCCCGGTGCTCTCCCACCGGTACTCAGTGGTCTGGTCCGAATCC

GAGAGAAGTAGATAGTGCAGAGGCCTGGGTTCTCAGCGGGCTTCTAGTGTGCCTTGGCTG
3961   ------------+---------+---------+---------+---------+---------+ 4020
       CTCTCTTCATCTATCACGTCTCCGGACCCAAGAGTCGCCCGAAGATCACACGGAACCGAC

TTCCTCCCTCACCTGCTGTCCTCCAGGGCTGGTTCCAGCATGCTCCCCCCTTTGAGGTGT
4021   ------------+---------+---------+---------+---------+---------+ 4080
       AAGGAGGGAGTGGACGACAGGAGGTCCCGACCAAGGTCGTACGAGGGGGGAAACTCCACA

TTGAGGGCCACCTCAGCTGCCTTGTGCTTGGCTGCCTTCTTGCTGGGGCCCTGACCTAAG
4081   ------------+---------+---------+---------+---------+---------+ 4140
       AACTCCCGGTGGAGTCGACGGAACACGAACCGACGGAAGAACGACCCCGGGACTGGATTC

AAAAGGGGCGTGGGCAATACTGGAGGTCACCGGCAGGACAGCAGAGAAACCAGCCCCCAC
4141   ------------+---------+---------+---------+---------+---------+ 4200
       TTTTCCCCGCACCCGTTATGACCTCCAGTGGCCGTCCTGTCGTCTCTTTGGTCGGGGGTG

AGCCTATCTCCTCATAGCCAGAGGGAGTGAGAAGAGCCCTCTGACCAACCTCCCCTGTCA
4201   ------------+---------+---------+---------+---------+---------+ 4260
       TCGGATAGAGGAGTATCGGTCTCCCTCACTCTTCTCGGGAGACTGGTTGGAGGGGACAGT

GAACTGGAAGGGTTCTACTAATTGTTGGACTAGCCTTTTTCCTAGTTAGCATTAACAGTC
4261   ------------+---------+---------+---------+---------+---------+ 4320
       CTTGACCTTCCCAAGATGATTAACAACCTGATCGGAAAAAGGATCAATCGTAATTGTCAG
```

FIG. 1D-5

```
       AACTTGGCACAACCTAGGATCTAAAAGGATCTGAAAGGAGAGCCTTAACTGAGGAATTGC
4321   ----------+---------+---------+---------+---------+---------+ 4380
       TTGAACCGTGTTGGATCCTAGATTTTCCTAGACTTTCCTCTCGGAATTGACTCCTTAACG

CTACATCAGCCTGGCCTGAGGGCATGTCTGGGGGTGGGTGGGGGGATGGACTGATAGTT
4381   ----------+---------+---------+---------+---------+---------+ 4440
       GATGTAGTCGGACCGGACTCCCGTACAGACCCCCACCCACCCCCCCTACCTGACTATCAA

AATTGATGCTGATATGCACAGCCCACTATTGTGGTACCACCCCTAGGCAGGTGGTCCTGA
4441   ----------+---------+---------+---------+---------+---------+ 4500
       TTAACTACGACTATACGTGTCGGGTGATAACACCATGGTGGGGATCCGTCCACCAGGACT

ACTGTGTAAGAAATCTAGTAGAGTATAAATAAGCCAGCCAGCCAGCATGGAGTATCTGCC
4501   ----------+---------+---------+---------+---------+---------+ 4560
       TGACACATTCTTTAGATCATCTCATATTTATTCGGTCGGTCGGTCGTACCTCATAGACGG

ATTGTTCCTGCTGTGCTTCTGTGGCTGTGAAGTGAGTTCCTTAGTCAGAAGTAGCAAGAA
4561   ----------+---------+---------+---------+---------+---------+ 4620
       TAACAAGGACGACACGAAGACACCGACACTTCACTCAAGGAATCAGTCTTCATCGTTCTT

TCAGATTATTTTCTTTGGTCTTGACTGATAATGTGAGTTTCTTCCTTAGCTTCCCTTAGT
4621   ----------+---------+---------+---------+---------+---------+ 4680
       AGTCTAATAAAAGAAACCAGAACTGACTATTACACTCAAAGAAGGAATCGAAGGGAATCA

CATGAATGTAACCTGAACTGTAAACCTATCAACCCTTTTCCTCCTCTAAACTGCTTTTAG
4681   ----------+---------+---------+---------+---------+---------+ 4740
       GTACTTACATTGGACTTGACATTTGGATAGTTGGGAAAAGGAGGAGATTTGACGAAAATC

TTTCGGAGCCTTACTACAGCAACAGAAATGGGCCTTGAACACCTCCTCTTTCAGTCAGCT
4741   ----------+---------+---------+---------+---------+---------+ 4800
       AAAGCCTCGGAATGATGTCGTTGTCTTTACCCGGAACTTGTGGAGGAGAAAGTCAGTCGA

CCCGTAATGAAACTGTGCCAGGCAGGATTTTTGAGCTCCAACACTGGTGGGTTGCGGAGG
4801   ----------+---------+---------+---------+---------+---------+ 4860
       GGGCATTACTTTGACACGGTCCGTCCTAAAAACTCGAGGTTGTGACCACCCAACGCCTCC

GATGTTTTGCTCTGTCTTTCTTTCCCCTTTTCTCTTCCCTCGGTAAATAGGAAATAGAGA
4861   ----------+---------+---------+---------+---------+---------+ 4920
       CTACAAAACGAGACAGAAAGAAAGGGGAAAAGAGAAGGGAGCCATTTATCCTTTATCTCT

CAACTGAGGGTCTGAAGTCAAAGCTCTGCTCTGCCACTTATTACATGTGAACTGGAGCCT
4921   ----------+---------+---------+---------+---------+---------+ 4980
       GTTGACTCCCAGACTTCAGTTTCGAGACGAGACGGTGAATAATGTACACTTGACCTCGGA

ACCATTTAATTTCTCATACTAAGTTCTTCGTGTTCAATGTGAGGCATGAAGGCTAGCAGA
4981   ----------+---------+---------+---------+---------+---------+ 5040
       TGGTAAATTAAAGAGTATGATTCAAGAAGCACAAGTTACACTCCGTACTTCCGATCGTCT

GTATGTGCTCCCCCTAATACCCACGAGGAGTTCAATGTCTCATTTACTCTTCCTCTGGGG
5041   ----------+---------+---------+---------+---------+---------+ 5100
       CATACACGAGGGGGATTATGGGTGCTCCTCAAGTTACAGAGTAAATGAGAAGGAGACCCC

TGATAAAGTAGCAGATCCGAATTC
5101   ----------+---------+----- 5124
       ACTATTTCATCGTCTAGGCTTAAG
```

FIG. 1D-6

```
          -405
        M TCCAGGAC.A TAATGCCCAA TTCTGACAGG AGTTTCTCCA .GTCAGGAAC
        R TCCAGGACTA TAATGCTCAA TCCTGACAGG AGTTTCTTCA .GTCAGGAAC
        H TAACCCCTCC TGACATGAGT TTCTTGTGCT TTAGTCTACA GGTTAGGAAA
Consensus TCCAGGAC-A TAATGC-CAA TTCTGACAGG AGTTTCT-CA -GTCAGGAAC
                                       AP1                    AP1
          -355
        M AAGAGGTGAT CAATTGAAGC TTCTCCAATC TGTTGAAGGA TTGGAGGTTC
        R AAGAGGTGAT CAATTGAAGC TTCTCCAACC TGTTGAAGGA TTGGAGGTTC
        H GAGGGGAAGT GATAAACAAG CTCTCCAACC TGTTGAGGGA TTAGGGGTTC
Consensus AAGAGGTGAT CAATTGAAGC TTCTCCAACC TGTTGAAGGA TTGGAGGTTC
                                       CMYB
          -305
        M TTCTAAGGTT CCCCCAGGGT CTAACTCTGA CAAACTGTCT GCAATTAATG
        R TTGTAAGACT CCTCCAGGGC CTAGCTCTGA CAAACTGTCT GCAATTAATA
        H GTCTAAGGCT CC.CCAGGGC CTGGCTCTGA CAAAGCGTCT GCAACTAATG
Consensus TTCTAAGGCT CC-CCAGGGC CTAGCTCTGA CAAACTGTCT GCAATTAATG
                                      AP1
          -255
        M ATGCTTCCTG AGCTCCGGAG ACAAGATTTA TGCATCTAAT AAAGTCTATA
        R ATGCTTCCTG AGCTCTGGAG ACAAGATTTA TGCATCTAAT AAAGTC..TA
        H ATGCTTCTTG AGCTCTGGAG ACAGGATTTA TGCATCTAAT AAAAGC..TG
Consensus ATGCTTCCTG AGCTCTGGAG ACAAGATTTA TGCATCTAAT AAAGTC--TA -205
        M TAACTCCAGG CTTA.GGCTG GGGGGGAGGA AGCTAAGAGC AGAGAGTCCC
        R TAACTCCAGG CTCA.TGCT. GGGGGTAGAG AACTGAGAGC AGAAAGTCTC
        H TAACTCCAGG CTTAGGGGCC GGGGGCAGGA GGCTGAGAGC ATGGAGT..C
Consensus TAACTCCAGG CTTA-GGCT- GGGGG-AGGA AGCTGAGAGC AGAAAGTC-C -155
        M CAGGGGAGTA CGGGAGGGGG GGTCCCAGGT GGCTCTTAAT AGAGCCATGC
        R CCAGGGCGGT ATGGGAGGGG GGTCCCAGGT GGCTCTTAAT AGAGCCATGC
        H CTGGGGGCGC CATGGGAGGA GATCCCAGGT GGCTCCTAAT .GAGCCCTGC
Consensus C-GGGG-GG- C-GGGGGGGG GGTCCCAGGT GGCTCTTAAT AGAGCCATGC
                                             NFkappaB/SP1
          -105
        M ATTTCCATTG CTTGTCTAGA TTTCCCCCCA GGCTGCCGGT GAGGTGGGGG
        R ATTTCCATTG CCTGTCTAGA TTT.CCCCCA GGCTGCTGAT GAGGTGGGGG
        H ATTTCATTTG CCTGCTCTAG ATTCCCCTAA GGCTACTGTG AGGCTGGGGG
Consensus ATTTCCATTG CCTGTCTAGA TTTCCCCCCA GGCTGCTG-T GAGGTGGGGG
             NFAT              NFAT
          -55
        M TA.GGG.ACA TCAGGTATAA GAAGACCGTG .GGCACTCAG GAGGCAGAT
        R TAGGGG.ACA TCAGGTATAA GAAGCCCGTG TGCCACGGAG GAGGCAGAT
        H TGGGGGAACA GCAGGTATAA GAGGTTGGGG TGGCTGTAGG AGGGTAGGT
Consensus TAGGGG-ACA TCAGGTATAA GAAG-CCGTG TGGCACT-AG GAGGCAGAT -5        +12
        M GCAGCATGGA CTCCAAG
        R GCAGCATGGA TTCCAAG
        H GCAGCATGGA TTCTAGG
Consensus GCAGCATGGA TTCCAAG
```

FIG. 3

```
        TGGCTTAGTCCGCATTAACAGAAATATGGTATCTGGAGCATCCAGATCCAAACCTGCTCT
-2480   ----------+----------+----------+----------+----------+----------+
        ACCGAATCAGGCGTAATTGTCTTTATACCATAGACCTCGTAGGTCTAGGTTTGGACGAGA

AATCTACGTGTCTAAAGGATAAGTTGGTTCCTAGATGCCTTGCCTTAAAGAGTGGGGTGC
-2419   ----------+----------+----------+----------+----------+----------+
        TTAGATGCACAGATTTCCTATTCAACCAAGGATCTACGGAACGGAATTTCTCACCCCACG

TTCCCCTTGAGCAAAAAAGACTATGGAGTGGGCCAGGTGCGGTGGCTCACGCCTGTAATC
-2359   ----------+----------+----------+----------+----------+----------+
        AAGGGGAACTCGTTTTTTCTGATACCTCACCCGGTCCACGCCACCGAGTGCGGACATTAG

CCAACACTTTGGGATGCCAAGGTGGGTGGATTGCTTGAGGTCAGGAGTTCAAGACCAGCC
-2299   ----------+----------+----------+----------+----------+----------+
        GGTTGTGAAACCCTACGGTTCCACCCACCTAACGAACTCCAGTCCTCAAGTTCTGGTCGG

TGGCCAACATGGTGAAACCCCATCTCTACTCCCCCTACAAAAATTAGCCGGGCATAGTGG
-2239   ----------+----------+----------+----------+----------+----------+
        ACCGGTTGTACCACTTTGGGGTAGAGATGAGGGGGATGTTTTTAATCGGCCCGTATCACC

TGTGTGCCTGTAATCCCAGCTACTTGGGAGGCTGAGGCAGGAGAATCGCCTGAACCCGGG
-2179   ----------+----------+----------+----------+----------+----------+
        ACACACGGACATTAGGGTCGATGAACCCTCCGACTCCGTCCTCTTAGCGGACTTGGGCCC

AGGCAGAGGGGTTGCGGTGAGCCGAGATCGCACCACTGCACTCCAGCCTGGGTGACAGAG
-2119   ----------+----------+----------+----------+----------+----------+
        TCCGTCTCCCCAACGCCACTCGGCTCTAGCGTGGTGACGTGAGGTCGGACCCACTGTCTC

CCAGACTCCATCGTAAAAAAAAAAAAAAAAAAGCTGGAGTGTAAGAATGAACTCTCTCTT
-2059   ----------+----------+----------+----------+----------+----------+
        GGTCTGAGGTAGCATTTTTTTTTTTTTTTTTTCGACCTCACATTCTTACTTGAGAGAGAA

CAAAAATATGAAGAGCTTTTACACATGAAAGAGATGAGATGTTCTGTTGAGACTTAATGG
-1999   ----------+----------+----------+----------+----------+----------+
        GTTTTTATACTTCTCGAAAATGTGTACTTTCTCTACTCTACAAGACAACTCTGAATTACC

AGCAAACTAAGACCCCGAGTAGAAGTCACAGGAAGCCCAAAGCCCCCTCGGCACAAGGAT
-1939   ----------+----------+----------+----------+----------+----------+
        TCGTTTGATTCTGGGGCTCATCTTCAGTGTCCTTCGGGTTTCGGGGGAGCCGTGTTCCTA

AAATATTGTCCGAAGACTGTCTGAGGAGATGGTAAGTTCCCCGACTGGGGCACATGAGGC
-1879   ----------+----------+----------+----------+----------+----------+
        TTTATAACAGGCTTCTGACAGACTCCTCTACCATTCAAGGGGCTGACCCCGTGTACTCCG

AATCACAGCTAACGTTTTGAGGATACCTGTTCTATGCAAGCTGTTTTATTGAATGGATTA
-1819   ----------+----------+----------+----------+----------+----------+
        TTAGTGTCGATTGCAAAACTCCTATGGACAAGATACGTTCGACAAAATAACTTACCTAAT

CAAAAGTATGTTAAGTAATGCACACCCTAGGAAGGCGTTCCTTGTAAAATGGGCCCATG
-1759   ----------+----------+----------+----------+----------+----------+
        GTTTTCATACAATTCATTACGTGTGGGATCCTTCCGCAAGGAACATTTTACCCGGGTAC

TTTCAGGTGAGGAAACTGAAGCTCAGAGCGGGAGACAGCTTGCTCAAGCAGAGGCCAAGG
-1699   ----------+----------+----------+----------+----------+----------+
        AAAGTCCACTCCTTTGACTTCGAGTCTCGCCCTCTGTCGAACGAGTTCGTCTCCGGTTCC

CCTTTACGTCATGGCTCTTCCTCAGCACAAGCTAGAGACCCACACTGGTGGGGATGCTCC
-1639   ----------+----------+----------+----------+----------+----------+
```

FIG. 4-1

```
         GGAAATGCAGTACCGAGAAGGAGTCGTGTTCGATCTCTGGGTGTGACCACCCCTACGAGG
         AAAAGGGACTCGAGGATTAGAAGGAACCTGCACCATATGGCTTGAAGGCCCTCTCCCTGA
-1579    ----------+---------+---------+---------+---------+---------+
         TTTTCCCTGAGCTCCTAATCTTCCTTGGACGTGGTATACCGAAACTTCCGGAGAGGGACT

GGATTAGTGATTCTGATTTTTCTTAAGACAGGATTCTAGGCTACTCTATATGAGAGCCAG
-1519    ----------+---------+---------+---------+---------+---------+
         CCTAATCACTAAGACTAAAAAGAATTCTGTCCTAAGATCCGATGAGATATACTCTCGGTC

GGCCAGGCAGAGGCTGTGGAGACCAGAGTCGGGGTCAGAATGATAGTCCAGCCCCACAGT
-1459    ----------+---------+---------+---------+---------+---------+
         CCGGTCCGTCTCCGACACCTCTGGTCTCAGCCCCAGTCTTACTATCAGGTCGGGGTGTCA

AGCCTGCTCCTGTCCTTCTGGGACTCCCTGGAGACTGGACCCTAGCACCTCCACTCAGCC
-1399    ----------+---------+---------+---------+---------+---------+
         TCGGACGAGGACAGGAAGACCCTGAGGGACCTCTGACCTGGGATCGTGGAGGTGAGTCGG

TCACCCTCCTCACTTCCTCTGCAGAGGTCTATTCTAGGAAAAGGAAATGGCCGGAGCTGG
-1339    ----------+---------+---------+---------+---------+---------+
         AGTGGGAGGAGTGAAGGAGACGTCTCCAGATAAGATCCTTTTCCTTTACCGGCCTCGACC

CAATGAGGAGCTGTGACCACAGGGTGGCAGCAGTGCTTCAGCTGTGGAGAGTGACTATAG
-1279    ----------+---------+---------+---------+---------+---------+
         GTTACTCCTCGACACTGGTGTCCCACCGTCGTCACGAAGTCGACACCTCTCACTGATATC

GAAGGGCGATGAGGCAGGTCGGAAGCAGTGCTCTCTAGTGAGGATGGGGGTCTGTCTGCA
-1219    ----------+---------+---------+---------+---------+---------+
         CTTCCCGCTACTCCGTCCAGCCTTCGTCACGAGAGATCACTCCTACCCCCAGACAGACGT

AAGATTGGAAGCCACACTCATTCAGTGGGCTCCAAAATCCTGTAGCCTCCCTCTATATCT
-1159    ----------+---------+---------+---------+---------+---------+
         TTCTAACCTTCGGTGTGAGTAAGTCACCCGAGGTTTTAGGACATCGGAGGGAGATATAGA

TAATAATTTTTTTTTTTGAGACAGAGTTTCTCTTTTTGCCAAGGCTGGAGTGTAGTGGT
-1099    ----------+---------+---------+---------+---------+---------+
         ATTATTAAAAAAAAAAAACTCTGTCTCAAAGAGAAAAACGGTTCCGACCTCACATCACCA

GCCATCTCAGCTCACTGCAACCTCTGCCTCCCCGATTCAAGCGATTCTCCTGCCTCAGCC
-1039    ----------+---------+---------+---------+---------+---------+
         CGGTAGAGTCGAGTGACGTTGGAGACGGAGGGGCTAAGTTCGCTAAGAGGACGGAGTCGG

TCCTGAGTAGCTGGGATTACAGGTGCCTACCACCACGCCCAGCTAATTTTTGTATTTTTA
-979     ----------+---------+---------+---------+---------+---------+
         AGGACTCATCGACCCTAATGTCCACGGATGGTGGTGCGGGTCGATTAAAAACATAAAAAT

GTAGACAGGGGTTTCACCATGTTGGCCAGGCTGGTCTCGAACTCCTGCCCTCAGGTGATC
-919     ----------+---------+---------+---------+---------+---------+
         CATCTGTCCCCAAAGTGGTACAACCGGTCCGACCAGAGCTTGAGGACGGGAGTCCACTAG

CACCCGCCTTGGTCTCCCAAAGTGCTGGGGTTACAGGTGTGAGGCACTGCACCCGGCAAA
-859     ----------+---------+---------+---------+---------+---------+
         GTGGGCGGAACCAGAGGGTTTCACGACCCCAATGTCCACACTCCGTGACGTGGGCCGTTT

AAAAAAATGGTTTTTAATTAAAAAAAAAAAGATACAGGCTGGGCATGGTGGTTGACGCCT
-799     ----------+---------+---------+---------+---------+---------+
         TTTTTTTACCAAAAATTAATTTTTTTTTTCTATGTCCGACCCGTACCACCAACTGCGGA

GTAGTCCCAGCTACTTGGGAGGCTGAGGCAGGAGAATCACTTGAACCCAGGAGCCAGAGG
-739     ----------+---------+---------+---------+---------+---------+
         CATCAGGGTCGATGAACCCTCCGACTCCGTCCTCTTAGTGAACTTGGGTCCTCGGTCTCC

TTGCAGTGAGCCGAGATCGCGCCACTGCACTCCAGCCTGGGCAAAAAGAGCGAAACTCCA
-679     ----------+---------+---------+---------+---------+---------+
```

FIG. 4-2

```
        AACGTCACTCGGCTCTAGCGCGGTGACGTGAGGTCGGACCCGTTTTTCTCGCTTTGAGGT
        TCTCAAAAGAAAAAAAGTTAAATTCTCTCCATCATCATGAAGTTGAATATATTTTTTCT
 -619   ----------+---------+---------+---------+---------+---------+
        AGAGTTTTTCTTTTTTTCAATTTAAGAGAGGTAGTAGTACTTCAACTTATATAAAAAGA

ATCCACAGGCAAATCTGAGTAGCCTCCAAGAGGCACACAAGCAGAGGATGGGCTGTGTTG
 -559   ----------+---------+---------+---------+---------+---------+
        TAGGTGTCCGTTTAGACTCATCGGAGGTTCTCCGTGTGTTCGTCTCCTACCCGACACAAC

CCCTGACTGCCAGCCCCAGGCACAGAGGACCAGGCCTGGTCATCCTCACAGACTCTGACC
 -499   ----------+---------+---------+---------+---------+---------+
        GGGACTGACGGTCGGGGTCCGTGTCTCCTGGTCCGGACCAGTAGGAGTGTCTGAGACTGG

CTGGCTCTTCCCACTCCTCTTCCACTCCAGGACATCCTACTTAACCCCTCCTGACATGAG
 -439   ----------+---------+---------+---------+---------+---------+
        GACCGAGAAGGGTGAGGAGAAGGTGAGGTCCTGTAGGATGAATTGGGGAGGACTGTACTC

TTTCTTGTGCTTTAGTCTACAGGTTAGGAAAGAGGGGAAGTGATAAACAAGCTCTCCAAC
 -379   ----------+---------+---------+---------+---------+---------+
        AAAGAACACGAAATCAGATGTCCAATCCTTTCTCCCCTTCACTATTTGTTCGAGAGGTTG

CTGTTGAGGGATTAGGGGTTCGTCTAAGGCTCCCCAGGGCCTGGCTCTGACAAAGCGTCT
 -319   ----------+---------+---------+---------+---------+---------+
        GACAACTCCCTAATCCCCAAGCAGATTCCGAGGGGTCCCGGACCGAGACTGTTTCGCAGA

GCAACTAATGATGCTTCTTGAGCTCTGGAGACAGGATTTATGCATCTAATAAAGTCTGTA
 -259   ----------+---------+---------+---------+---------+---------+
        CGTTGATTACTACGAAGAACTCGAGACCTCTGTCCTAAATACGTAGATTATTTCAGACAT

ACTCCAGGCTTAGGGGCCGGGGGCAGGAGGCTGAGAGCATGAAGTCCTGGGGGCGCCATG
 -199   ----------+---------+---------+---------+---------+---------+
        TGAGGTCCGAATCCCCGGCCCCCGTCCTCCGACTCTCGTACTTCAGGACCCCCGCGGTAC

GGAGGAGATCCCAGGTGGCTCCTAATGAGCCCTGCATTTCATTTGCCTGCTCTAGATTCC
 -139   ----------+---------+---------+---------+---------+---------+
        CCTCCTCTAGGGTCCACCGAGGATTACTCGGGACGTAAAGTAAACGGACGAGATCTAAGG

CCTAAGGCTACTGTGAGGCTGGGGGTGGGGGAACAGCAGGTATAAGAGGTTGGGGTGGCT
 -79    ----------+---------+---------+---------+---------+---------+
        GGATTCCGATGACACTCCGACCCCCACCCCCTTGTCGTCCATATTCTCCAACCCCACCGA

GTAGGAGGGTAGGTGGCAGC
 -19    ----------+---------+
        CATCCTCCCATCCACCGTCG
```

FIG. 4-3

```
-4236 GTATCTATGAATATAGCTCTGTTCTATATCCTTTTGACATGTAGCAATAC
        M  N  I  A  L  F  Y  I  L  L  T  C  S  N  T

-4186 CTCTCCATCCTCAAGGAACTCAACCCAGTCTGGGTCTCCCCAGGCTCCAG
       S  P  S  S  R  N  S  T  Q  S  G  S  P  Q  A  P  V

-4136 TGGTAGACTCTGACAGGTGGGAGGATACAGTGCTCTGGGCTGTTTTGTTA
       V  D  S  D  R  W  E  D  T  V  L  W  A  V  L  L

-4086 CAAAAGTGTCTTCTGTCCTTTCCCTCCTCCCAATTCAGCATGACCCCTGT
       Q  K  C  L  L  S  F  P  S  S  Q  F  S  M  T  P  V

-4036 GAGCAGGCTCTCACAATCTCCTGGGGCAGGGCTGAGGCAGGGGCTTTCAG
       S  R  L  S  Q  S  P  G  A  G  L  R  Q  G  L  S  A

-3986 CTCTTCTCCATAACTATCCCTTCTTCCTTCCCCCATGCCATTTAGCAGTT
       L  L  H  N  Y  P  F  F  L  P  P  C  H  L  A  V

-3936 ATCACCCAGCCTTGCCTTCTCCCTCCATCCCTTGCCCTGACATATACTGT
       I  T  Q  P  C  L  L  P  P  S  L  A  L  T  Y  T  V

-3886 GCCTTATTTATGCTGCAAATATAACATTAAACTATCAAGAGAATGA
       P  Y  L  C  C  K  Y  N  I  K  L  S  R  E
```

PROMOTER FOR NEUROPEPTIDE FF AND USE THEREOF FOR THERAPY AND DIAGNOSTICS

CROSS REFERENCE TO RELATED APPLICATIONS

This application is a continuation-in-part of application Ser. No. 09/365,755, filed Aug. 3, 1999, now abandoned, which is incorporated herein by reference.

FIELD OF THE INVENTION

The present invention relates to sequencing and cloning of the 5'-flanking region of neuropeptide FF (NPFF) promoter. A neuropeptide FF (NPFF) promoter region for mouse, rat and human has been cloned and sequenced. The characterized neuropeptide FF (NPFF) promoter is useful in screening and treating for genetic diseases associated with the promoter area of the NPFF gene by modulation of activation or inhibition of NPFF gene expression through the regulatory sites in the promoter area. The promoter can also be used as a marker for its locus in the corresponding chromosome. Thus, the characterized promoter is of considerable diagnostic value and can be used in gene therapy and in DNA analyses. Further, the promoter can be used for developing genetically modified animals.

BACKGROUND OF THE INVENTION

Neuropeptide FF was originally identified as a mammalian counterpart of the molluscan cardioactive peptide FMRF-amide (Yang et al., 1985), found in the superficial dorsal horn of the spinal cord, hypothalamus, medulla and pituitary gland (Kivipelto et al. 1989). The findings that the peptide is present in the hypothalamo-pituitary system, decreases during salt-loading and is deficient in the pituitary gland of vasopressin-deficient Brattleboro rats, implicate NPFF involvement in hypothalamic regulation of pituitary functions (Majane and Yang, 1991; Majane and Yang, 1990; Majane et al., 1993). Peripherally administered NPFF raises blood pressure in rats, an effect mediated by both peripheral and central mechanisms (Allard et al., 1995; Laguzi et al., 1996). NPFF has also been implicated in sensory systems, most notably pain and morphine analgesia (Yang et al., 1985). Intracerebroventricular NPFF has been reported to induce a vigorous abstinence syndrome in morphine-tolerant rats. NPFF has attenuated the antinociceptive effects of morphine when administered in the third ventricle, whereas intrathecal NPFF produces long-lasting antinociception (Gouarderes et al., 1993).

The NPFF gene is located in the human chromosome locus 12q13 (Burke et al. 1998), which is known to be associated with a severe condition referred to as Allgrove syndrome (triple-A syndrome). The current NPFF promoter area is an evident region where mutations responsible for triple A syndrome are located. It serves as a useful marker for the appropriate area of chromosome 12, and has diagnostic and therapeutical value in treatment of a triple-A syndrome.

SUMMARY OF THE INVENTION

Accordingly, it is an object of this invention to clone and sequence the 5'-flanking region of the NPFF promoter in human, rat and mouse.

The promoter region cloned and characterized here plays an essential role in etiology and/or pathogenesis of CNS disorders involving NPFF, including those associated with deficient regulation of autonomic function, pain conditions, and hormonal dysfunction. Accordingly, another object of the invention is to provide potential methods of screening and treating for genetic diseases associated with the promoter area of the NPFF gene by modulation of activation or inhibition of NPFF gene expression through the regulatory sites in the promoter area. The sequence can also be used as a marker for its locus in the corresponding chromosome. Thus, the characterized promoter is of considerable diagnostic value and can be used in gene therapy and in DNA analyses.

Another object of the invention is to provide genetically modified animals.

BRIEF DESCRIPTION OF THE FIGURES

FIG. 1B shows the nucleotide sequence of the 5'-flanking region of the mouse NPFF gene (SEQ ID NO:6). Sequence is numbered relative to the translational start site (indicated by a bent arrow). The consensus TATA box is shaded. The putative regulatory elements are indicated by arrows underneath the sequences. The AC dinucleotide repeat is indicated by a thick bar under the sequence.

FIG 1C shows: Mouse NPFF promoter sequences. Nucleotide sequence from −9840 bp to −1 bp relative to the translational start site. cDNA sequence is underlined (SEQ ID NO: 1).

FIG 1D shows: Mouse genomic NPFF sequences from coding region and the 3' end of the gene. Nucleotide sequence from +1 relative to the translational start site. cDNA sequence is underlined (SEQ ID: 2).

FIG. 3 shows a comparison between the first 400 bp of the NPFF promoter from mouse (SEQ ID NO: 7), rat (SEQ ID NO: 8) and human (SEQ ID NO: 9) and a consensus sequence (SEQ ID NO: 10). Sequence similarity is about 90% between mouse and rat and about 70% between rat and human. Conserved consensus binding sites for transcription factors are marked under the sequence. The translational start site is marked by a bent arrow and the TATA-box is marked by a box. M=mouse, R=rat and H=human.

FIG. 4 shows: Nucleotide sequence of the human NPFF promoter. Nucleotide sequence from −2480 bp to −1 bp relative to the translational start site (SEQ ID NO: 3).

FIG. 5 shows: A new, previously unidentified open-reading frame was found in the mouse promoter residing from −4236 to −3841 relative to the translational start site. Amino acids are marked under the sequence (SEQ ID NO: 4). This protein (SEQ ID NO:5) may have multiple functions and it may give rise to a previously unidentified bioactive peptides.

DETAILED DESCRIPTION OF THE INVENTION

We report here the cloning of the 5'-flanking region of the NPFF gene from mouse, rat and human. Totally 9.8 kb, 1.5 kb and 1.3 kb of the NPFF promoter from mouse, rat and human was cloned and sequenced. Comparisons between the promoter region from all species showed a high sequence similarity. Such a high sequence homology and well-conserved structure could indicate an important physiological function and a need for a similar, tightly regulated transcription of the gene. We have previously shown that the NPFF gene is expressed in specific regions in the brain and in the spinal cord and is induced upon inflammatory stimulus (Vilim et al., 1999). In agreement with this several inflammation related transcription factor consensus sites were found (FIG. 1B), amongst them e.g. NFκB, which is considered as an immediate early mediator of immune and inflammatory responses (Lenardo & Baltimore, 1989). Also several consensus sites for the nuclear factor of activated T-cells (NFAT) were found (for review see Kel et al., 1999). Transcription factors belonging to this growing family play key roles in the regulation of cytokine and other genes during immune response. An interesting finding was also the consensus site in mouse and rat for heat shock factor 1 (HSF1). HSF1 is activated in cells exposed to elevated temperatures and other environmental stress conditions (Sarge et al., 1993). We also focused on the potential involvement of AP1, STAT1 and CREB.

Figure 2A:
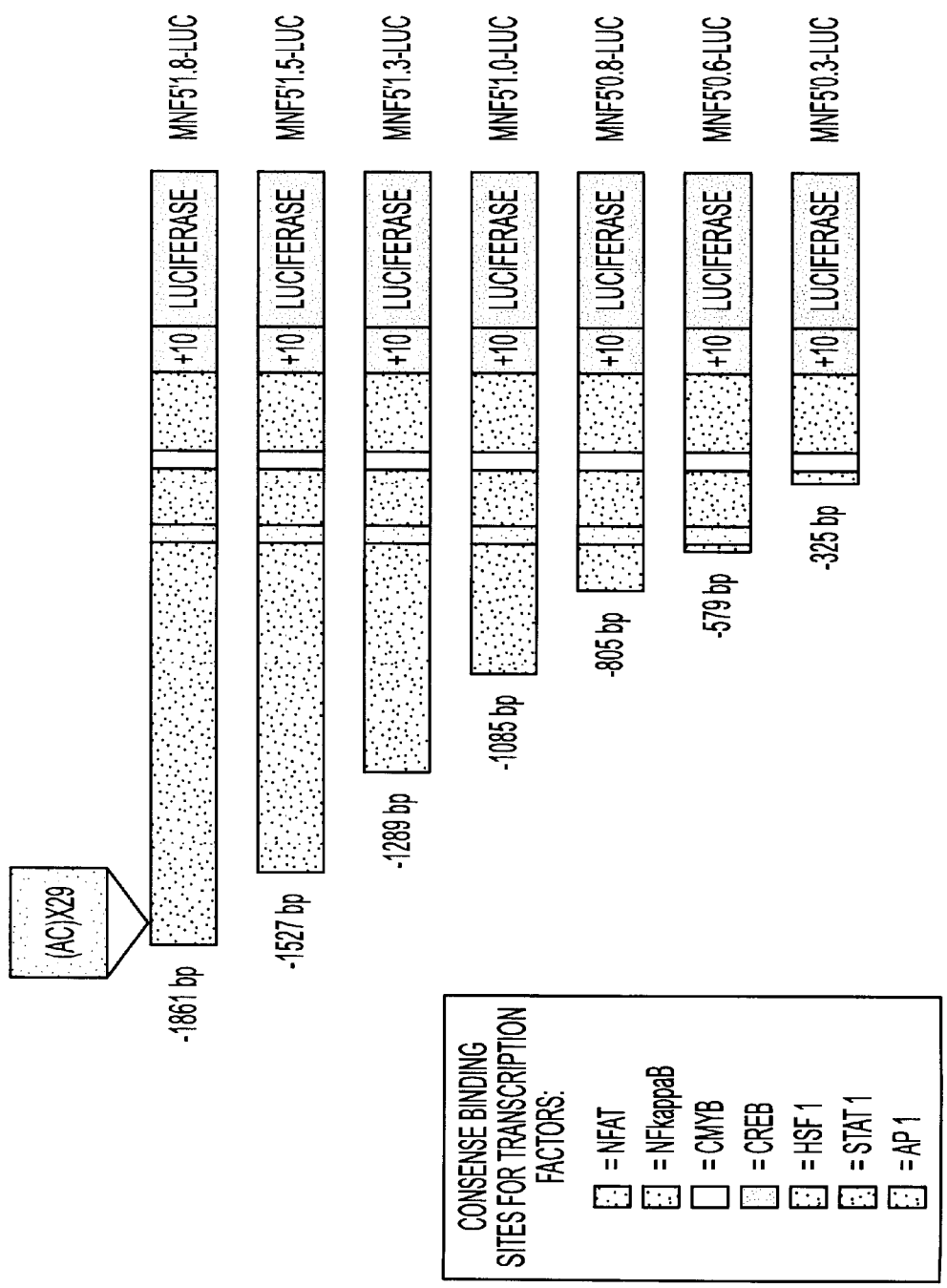
FIG. 2A shows a map of mouse NPFF promoter deletions fused to luciferase reporter gene. The numbers indicate the nucleotide positions of the 5'-untranslated region with the first nucleotide of the codon for initiation of translation as +1. The promoter fragments were subcloned in NheI-SmaI site of the promotorless luciferase vector pGL3 basic. The MNF5'1.8-LUC reporter construct contains a dinucleotide repeat. Consensus binding sites for transcription factors are indicated by gray-scale colours.
Figure 2B:
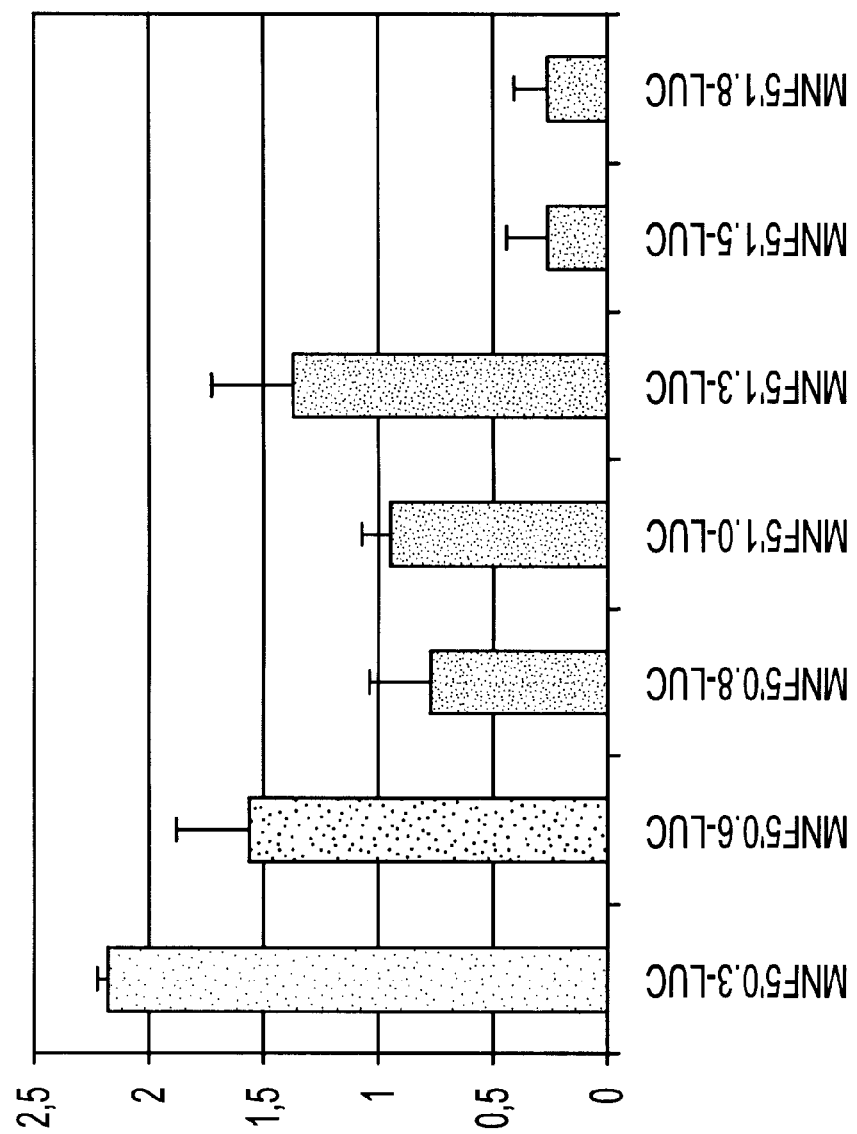
FIG. 2B shows: Basal activity of mouse NPFF promoter to drive luciferase expression. A549 cells were transiently transfected for 48 hours with 5'-promoter deletion constructs fused with a promoterless luciferase vector (pGL3 basic). Transfections were done in duplicate and repeated at least three times. The activity of the promoter was seen to vary with the highest activity in the shortest construct MNF5'0.3-LUC. The activity was seen to drop to almost unmeasurable levels in the MNF5'1.5-LUC construct. The activity was still minimal in the following MNF5'1.8-LUC construct.
Figure 2C:
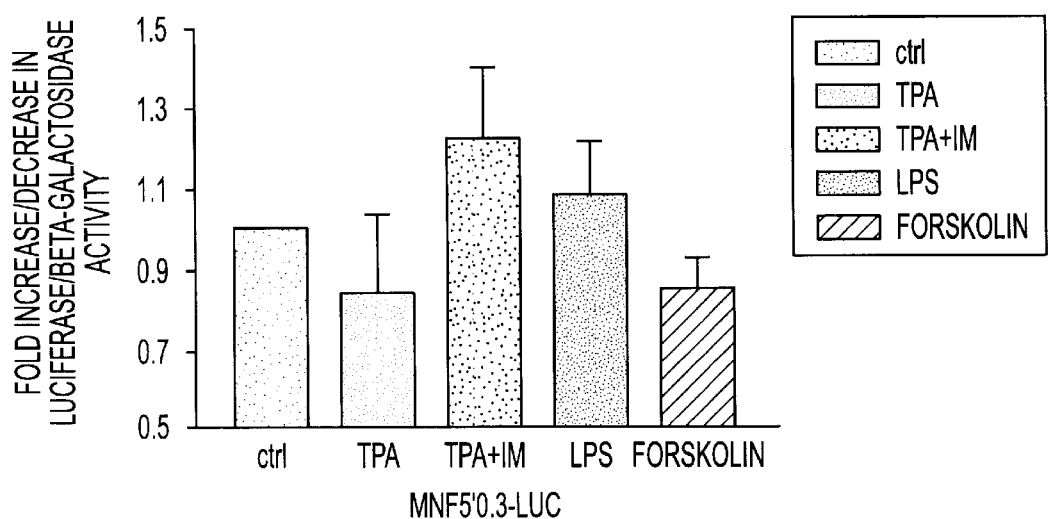
FIGS. 2C and 2D show: Activity analysis of the two shortest mouse NPFF promoter constructs MNF5'0.3-LUC and MNF5'0.6-LUC. A549 cells were transiently transfected for 24 hours whereafter the transfectants were stimulated for 16 hours with 10 nM TPA, 10 nM TPA and 1 $\mu$M ionomycin (IM), 15 $\mu$g/ml LPS or 10 $\mu$M forskolin. Unstimulated transfectants serve as control. Activity was seen to increase with ~30% in TPA+IM stimulated MNF5'0.3-LUC transfected cells. A slight increase in activity in the same transfectants was also seen with LPS stimulation. In cells transfected with MNF5'0.6-LUC a ~50% increase in activity was seen after TPA+IM stimulation. LPS stimulated transfectants also gave an at least ~40% increase in activity.
Figure 2D:
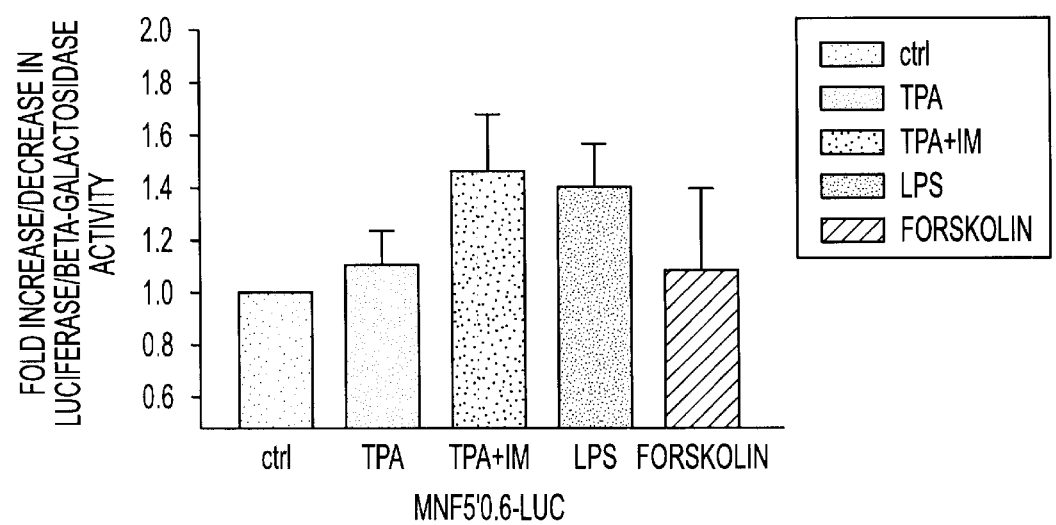

By using transiently transfected cells with deletional series of mouse NPFF promoter fused with firefly luciferase cDNA we could show that the basal activity of the promoter changes with increasing promoter size (FIG. 2B). This indicates that the promoter is tightly regulated is affected by several transcriptional factors and apparently has a complex transcriptional control. To study the possible involvement of some transcription factors our attempt was to a) activate transcription factors by protein kinase C (PKC) b) activate NFATp by PKC and $Ca^{2+}$-levels with TPA and ionomycin (Verweij et al., 1990), c) activate transcription factors by the bacterial endotoxin LPS and d) activate CREB by increasing intracellular cAMP values with forskolin. TPA and ionomycin increased promoter activity in MNF5'0.3-LUC transiently transfected cells (FIG. 2C). In this promoter region a consensus binding site for NFAT was also detected by computational analysis (FIG. 2A). It seems likely that this consensus binding site is active and that the transcription factor NFAT contributes to the transcriptional regulation of the NPFF gene. When MNF5'0.6-LUC was transiently transfected in cells and transfectants were stimulated both TPA and ionomycin and LPS stimulated cells showed higher promoter activity compared to control (FIG. 2D). This still confirms the involvement of NFATp and also possibly confirms the function of a NFκB or a STAT1 site residing in this construct (FIG. 2A). An interesting and contradictory finding was that although LPS seems to increase promoter activity, TPA does not. It seems likely that the transcriptional regulation is dependent on a synergistic mechanism involving several transcriptional factors affecting the gene expression.

A possible silencer element was also found in the proximal mouse promoter residing between 1.5 kb to 1.8 kb. Promoter activity dropped dramatically in cells transiently transfected with MNF5'1.5-LUC if compared with cells transfected with the construct MNF5'1.3-LUC, which is only about 200 bp shorter than MNF5'1.5-LUC. A possible silencer could accordingly reside between 1.3 and 1.5 kb of the mouse NPFF promoter. This finding is also confirmed by that cells transiently transfected with the longest construct. MNF5'1.8-LUC, also exhibits a similarly low promoter activity. It would be interesting to see if a longer promoter construct than the ones used in this study could again raise the promoter activity. Since we have cloned and sequenced also the corresponding region in the rat NPFF promoter and the sequence similarity was about 90%, it is possible that this region could be a functional, cell-specific silencer. It still remains unknown if the human NPFF promoter contains similar sequence. The possibility also remains that the AC-dinucleotide repeat in the MNF5'1.8-LUC construct adds additional regulatory effects. Additional roles of the AC-repeat might also be possible since an almost complementary GT-repeat was found approx. 6.5 kb upstream from the TATA-box in the mouse promoter. These partially complementary elements might interact to form complex secondary structures that may in turn contribute to the regulation of this promoter. Similar AC-repeat structures have been characterized in some other brain specific promoters such as PAX-6 gene (Okladnova et al., 1998) and the GLYT-1 gene (Borowsky & Hoffman, 1998). Proteins bound to repeat elements has been reported (Xu & Goodridge, 1998). Thus it is possible to identify this/these proteins bound to the AC-repeat which may play a role in control of the function of the AC-repeat. These proteins might control the accessability of the AC-segment to the complementary GT-repeat.

To study the endogenous NPFF promoter activity in vitro, we tried to affect the transcription of the gene by stimulating a cell-line, A549, which has been found to endogenously express NPFF mRNA. The results are in accordance with the transfection results; the expression of NPFF increased with LPS stimulation, which also was seen in the transfection results. This additionally emphasises the role of $NF_κB$ in the transcriptional regulation of the NPFF gene. The involvement of $NF_κB$ was also confirmed by decreased expression in cells stimulated first with TPA and then with the known $NF_κB$ inhibitor $PGA_1$.

As a conclusion, current data shows that the transcriptional regulation of the NPFF gene is highly complex and probably involves several transcription factors in synergy in control of the gene expression.

It is obvious that key elements involved in regulation of the NPFF gene are included in the characterized promoter, which has not been reported earlier. NPFF is involved in autonomic regulation including blood pressure and heart functions, analgesia and morphine tolerance, learning, and its expression is increased in the spinal cord after peripheral inflammation. Modulation of activation or inhibition of NPFF gene expression through the regulatory sites in the promoter area may be a part of pathophysiology in disease conditions related to these conditions.

The NPFF gene is located in the human chromosome locus 12q13 (Burke et al. 1998), which is known to be associated with a severe condition referred to as Allgrove syndrome (triple-A syndrome) characterized by a triad of adrenocorticotropic hormone (ACTH), resistant adrenal insufficiency, achalasia and alacrima, hypoglycaemia and sensory impairment and autonomic neuropathy. The current NPFF promoter area is an evident region where mutations responsible for triple A syndrome are located. Thus, the characterized promoter serves as a useful marker for the appropriate area of chromosome 12. Also in other applications it is of considerable diagnostic value and can be used in gene therapy and in DNA analyses.

The invention will be further described with reference to the following non-limiting examples.

EXAMPLE 1
Cloning of the Mouse NPFF Promoter

Stratagene mouse genomic library was screened with mouse NPFF cDNA (Vilim et al., 1999). DNA from positive clones were isolated, digested with a panel of restriction enzymes and analysed by Southern blotting. A 4.3 kb EcoRI DNA fragment (see FIG. 1A) that hybridized with the mouse NPFF cDNA probe was subcloned in pBluescript KS+/− vector (Stratagene). The cloned 4.3 kb EcoRI fragment was sequenced by automated sequencer (ABI Prism Automated Fluorescence Sequencer) by using universal primers (T3, T7, Promega) and gene specific primers. Restriction enzyme map of the resulting sequence was computed by using the University of Wisconsin GCG Sequence Analysis Software Package. A 0.8 kb BamHI-EcoRI fragment at the 3'-end of the 4.3 kb EcoRI fragment was subsequently used to probe the Southern blot of NPFF lambda-DNA. This probe hybridized to a 4.4 kb fragment of BamHI-EcoRI digested NPFF lambda-DNA. The 4.4 kb BamHI-EcoRI fragment was thereafter subcloned in pBluescript KS+/− and sequenced as described previously. A 3.5 kb EcoRI-BamHI fragment located at the 5' end of the 4.3 kb EcoRI fragment was then used to reprobe the NPFF Southern. This probe hybrized to a 5.5 kb BamHI fragment, which in turn, was subcloned in pBluescript KS+/− and sequenced. A 2.5 kb BamHI-XbaI fragment at the 5'-end of the 5.5 kb BamHI fragment was finally used to reprobe the NPFF Souther filter and it hybridized to a 7 kb XbaI fragment. The 7 kb XbaI fragment was subsequently subcloned in pBluescript KS+/− and sequenced. The resulting nucleotide sequences were assembled using the GCG Sequence Analysis Software Package. Total of 10.3 kb of the NPFF promoter was cloned and sequenced. The search for the consensus transcription factor recognition sites was performed by MatInspector Professional from Transfac Database at NCBI/NIH.

Figure 1A:
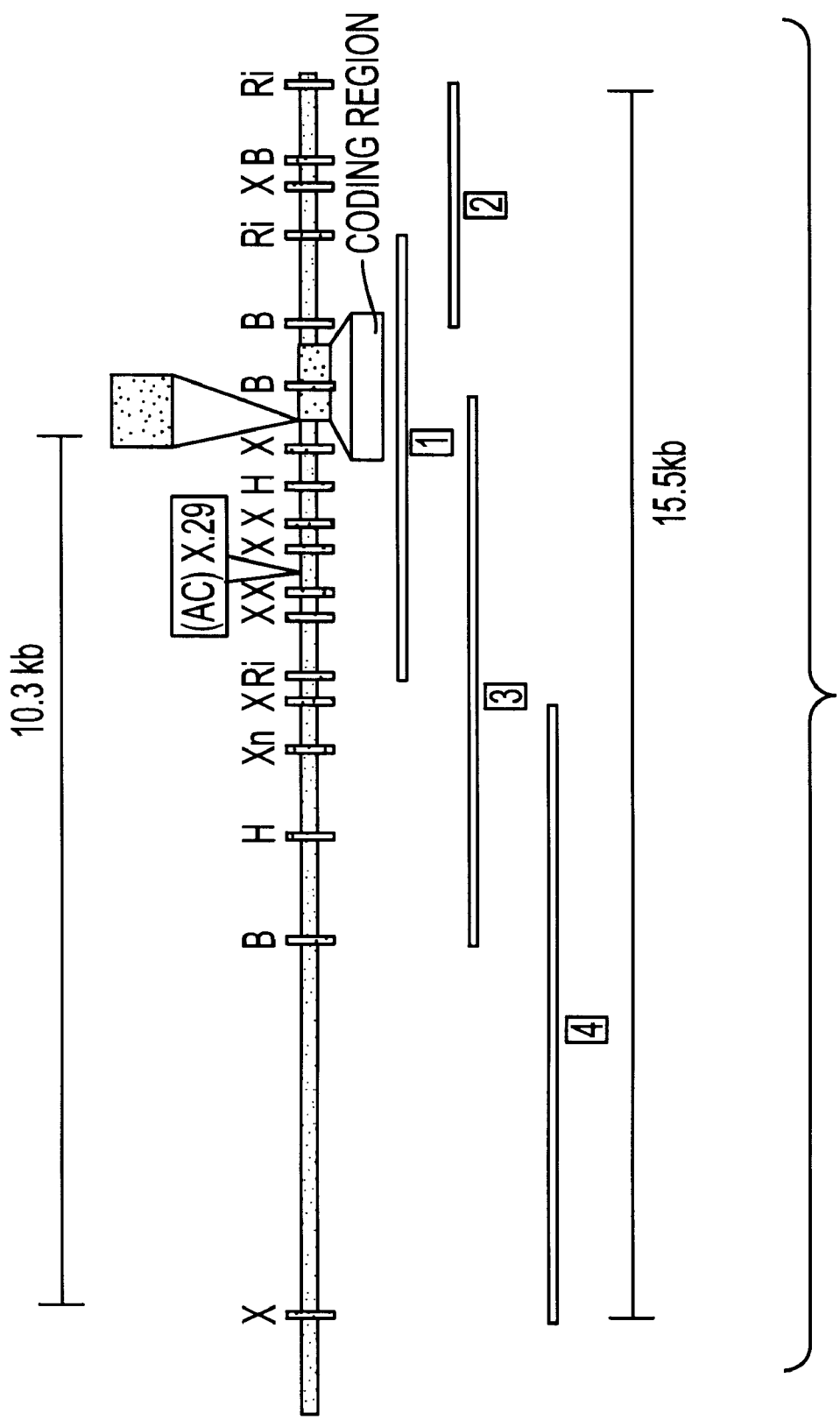
FIG. 1A is a schematic representation of the gene structure and cloning strategy for the mouse NPFF gene. Cutting sites for restriction enzymes are indicated by the following abbreviations: B=BamHI, H=HindIII, RI=EcoRI, X=XbaI and Xh=XhoI. The cloning strategy is marked by numbers 1–4. Bar 1 indicates the 4.3 kb EcoRI DNA fragment, bar 2 indicates the 4.5 kb BamHI-EcoRI DNA fragment, bar 3 indicates the 5.5 kb BamHI DNA fragment and bar 4 indicates the 7 kb XbaI DNA fragment.

By using the strategies presented in examples 1 and 4 a 9.8 kb, 1.5 kb and 1.3 kb piece of the NPFF promoter region was cloned and sequenced from mouse, rat and human, respectively. An illustration of the cloning strategy of the mouse NPFF promoter is shown in FIG. 1A. The homology between the proximal promoter based on sequence similarity was seen to be high between all species when doing comparisons based on computorial software (GCG, Wisconsin/ CSC, see FIG. 1B). Some of the consensus binding sites for transcription factors were seen to be conserved between all three species in the proximal promoter (FIG. 3).

EXAMPLE 2
Luciferase Reporter Constructs

To prepare 5'-deletion constructs of the proximal mouse promoter a 325 bp, 579 bp, 805 bp, 1085 bp, 1289 bp, 1527 bp and a 1861 bp fragment were amplified by PCR with the antisense primer 5'-TGG AGT CCA TGC TGC CAT-3' (SEQ ID NO: 11) and the sense primers (cutting site for NheI is underlined) 5'-GT<u>GCTA GC</u>A ATC TGT TGA AGG ATT GG-3' (SEQ ID NO: 12), 5'-GT<u>G CTAGC</u>A GTC TCC TAT CTC TCA CT-3' (SEQ ID NO: 13), 5'-GT<u>G CTA GC</u>A GAC GGA ACT GGA AAA AT-3' (SEQ ID NO: 14), 5'-GT <u>G CTA GC</u>T CTC CTA GCA AGT AAT TC-3' (SEQ ID NO: 15), 5'-GT<u>G CTA GC</u>T ACA TAT GAC TGA GAG AT-3' (SEQ ID NO: 16), 5'-GT<u>G CTA GC</u>A GCC TGG ATG CAT TGT AT-3' (SEQ ID NO: 17) and 5'-GT<u>G CTA GC</u>A CAG AGT CTC AGG CTT AG-3' (SEQ ID NO: 18), respectively. PCR reactions were performed with Pfu DNA polymerase (Promega) using an Eppendorf Mastercycler gradient machine with the following program: 1. 95° C. for 2 min, 2. 95° C. for 45 sek, 3. 53.6° C. for 30 sek, 4. 72° C. for 3 min with a 1 sek addition after each cycle, 5. Steps 2–4 for 35 cycles followed by a 72° C. 5 min final extension. The PCR products were cleaned from primers and nucleotides with QIAquick PCR purification kit (Qiagen) and subsequently cut with NheI. The cut products were run on a 1.2% agarose gel, excised from the gel and extracted by QIAquick agarose gel extraction kit. The PCR products were ligated in NheI-SmaI cut promoterless pGL3-basic vector (Promega) upstream of the firefly luciferase cDNA in sense orientation. The yielded constructs MNF5'0.3-LUC, MNF5'0.6-LUC, MNF5'0.8-LUC, MNF5'1.0-LUC, MNF5'1.3-LUC, MNF5'1.5-LUC and MNF5'1.8LUC (see FIG. 2A) were transformed in competent DH5α cells.

EXAMPLE 3
Transfection and Luciferase Assay

The functioning of the promoter in a cell was shown.

The human lung carcinoma A549 cell-line was kept in a humidified cell-incubator at 37° C. and with 5% $CO_2$. The cell-line was grown in Dulbecco's modified eagle medium (Gibco) containing 10% fetal calf serum (Gibco), 1×Glutamax (Gibco), 50 µg/ml penicillin and 50 IU/ml streptomycin (Gibco) and was regularly passed. 16–24 hours before transfection cells were plated at a density of $1 \times 10^5$ cells in 1 ml medium in 12-well dishes (Nunc). Reporter constructs (1 µg) or promoterless pGL3-basic vector (1 µg, as negative control) were co-transfected with pSV-β-galactosidase vector (0.5 µg, Promega) by first mixing 3 µl of Fugene 6 (Roche) transfection reagent with 57 µl of serum-free medium, which was incubated at RT for 5 minutes. The mix was added to the DNA and incubated at RT for 15 minutes and then added to the cells. The transfections were done in duplicates and repeated at least three times. Cells were transiently transfected for a total time of 48 h and before collecting the transfectants some cells were left unstimulated or stimulated for 16 hours with TPA (10 nM), TPA (10 nM) and ionomycin (1 µM), lipopolysaccharide (LPS, 15 µg/ml) or forskolin (10 µM). Cells were collected and lysed with 140 µl of reporter lysis buffer (Promega) according to the manufacturer's manual. The luciferase assay was performed on 20 µl of cleared cell extract and 100 µl of luciferase assay reagent (Promega)

using a Luminoscan luminometer (Labsystems). Transfection efficiencies were determined by using β-Galactosidase enzyme assay system (Promega) with 50 µl of cell extract. The luciferase acitivity of each transfection was expressed as luciferase activity/β-galactosidase activity.

The ability of a deletional series of the NPFF promoter to drive the transcription of firefly luciferase cDNA is presented in FIG. 2B. The highest expression of luciferase was seen in the shortest construct (MNF5'0.3-LUC) with decreasing activity in the two following constructs (MNF5'0.6-LUC and MNF5'0.8-LUC, respectively). The luciferase expression started increasing again with the two following constructs (MNF5'1.0-LUC and MNF5'1.3-LUC, respectively) whereafter the expression decreased to barely measurable level with the last two constructs (MNF5'1.5-LUC and MNF5'1.8-LUC). The last construct also contained a 29×(AC) dinucleotide repeat.

To study the involvement of some known pro-inflammatory transcriptional factors the two shortest constructs (MNF5'0.3-LUC and MNF5'0.6-LUC) were transfected in cells and stimulated with a phorbol ester, a phorbol ester together with a $Ca^{2+}$-ionophore, a bacteria endotoxin and a cAMP activator. These compounds should all affect several transcription factors, amongst them many known pro-inflammatory transcription factors eg. $NF_\kappa B$, NFAT and CREB. The results are presented in FIGS. 2C and 2D. The results show an increase in luciferase activity of TPA and ionomycin stimulated MNF5'0.3-LUC transfected cells (FIGS. 2C and D) and an increase in luciferase activity in TPA and ionomycin and LPS stimulated MNF50.6'-LUC transfected cells.

EXAMPLE 4
Cloning of the 5'-flanking Region of the Human and Rat NPFF Gene Promoter To clone the promoter region of the human and rat NPFF gene, a Genome Walker kit (Clontech, Palo Alto, Calif.) was used according to manufacturer's instructions. The NPFF specific human and rat antisense primers used for the primary PCR reaction was 5'-GCT GCC ACC ACC TAC CCT CCT AC-3' (SEQ ID NO: 19) and 5'-CAC CCC AGC TCC CTG CCT CTT-3' (SEQ ID NO: 20), respectively. The antisense primer for the nested human and rat PCR was 5'-GTG GAT CCA TCT AGA GCA GGC AAA TG-3' (SEQ ID NO: 21) and 5'-CGT GGC CCC AGT TCC TCA GCA-3' (SEQ ID NO: 22), respectively. The PCR reactions were performed using a MJ Research MiniCycler. The primary PCR reactions was performed with the following conditions: 94° C. for 25 sec and 72° C. for 4 min×7 cycles; 94° C. for 25 sec and 67° C. for 4 min×32 cycles, followed by a 67° C. 4 min final extension. The nested PCR reactions was conducted using a 50 times diluted primary PCR product as a template, the same reaction composition and cycle parameters, except that nested primers were used and that 20 thermocycles were performed instead of 32. Using this technique, we were able to identify a single major PCR product in one of the human libraries (PvuII) and two major PCR products in the rat libraries (DraI and PvuII) provided in the Genome Walker kit. The products were purified with the QIAquick PCR purification kit (Qiagen) and cloned into pGEM T-vector (Promega) and sequenced automatically in both directions (ABI Prism Automated Fluorescence Sequencer). Using this approach 1.3 kb of the human NPFF promoter and 1.5 kb of the rat NPFF promoter was cloned and sequenced. We still continued our cloning efforts conserning the human NPFF promoter and by using a second round of the same approach as above we were able to clone an additional 4 kb fragment of the human promoter. Sequencing is now in progress. A comparison between the NPFF promoters from all species is presented in FIG. 3. The search for the consensus transcription factor recognition sites was performed by MatInspector and MatInspector Professional from Transfac Database at NCBI/NIH. Comparisonal studies to study homology between the NPFF promoters were performed using Seqweb software package available at CSC web site (www.csc.fi).

The human sequences have been presented in FIG. 4.

EXAMPLE 5
Comparison of Proximal Promoter of NPFF Gene Between Mouse, Rat and Human A comparison between the first 400 bp of the NPFF promoter from mouse, rat and human. Sequence similarity is about 90% between mouse and rat and about 70% between rat and human. Conserved consensus binding sites for transcription factors are marked under the sequence. The translational start site is marked by a bent arrow and the TATA-box is marked by a box (FIG. 3). M=mouse, R=rat and H=human.

The invention has been illustrated by examples and embodiments, but it may be varied in many ways. Such variations are not to be regarded as a departure from the spirit and scope of the invention and all such modifications are intended to be included within the scope of the enclosed claims.

References

Allard, M., Labrouche, S., Nosjean, A. & Laguzzi, R. (1995). Mechanisms underlying the cardiovascular responses to peripheral administration of NPFF in the rat. *J. Pharmacol. Exp. Ther.* 274: 577–583.

Burke, J. F., Clarke, A. J. H., James, M. R. & Perry, S. J. (1998). Physical mapping of the human NPFF gene and investigation of its candidacy as a disease gene locus. *Soc. Neurosci. Abstr.* 24(2): 2046.

Gouarderes, C., Sutak, M., Zajac, J. M. & Jhamandas, K. (1993). Antinociceptive effects of intrathecally administered F8Famide and FMRFamide in the rat. *Eur. J. Pharmacol.* 237:73–81.

Kel, A., Kel-Margoulis, O., Babenko, V. & Wingender, E. (1999). Recognition of NFATp/AP-1 composite elements within genes induced upon the activation of immune cells. *J. Mol. Biol.* 288: 353–376.

Kivipelto, L., Majane, E. A., Yang, H. Y. & Panula, P. (1989). Immunohistochemical distribution and partial characterization of FLFQPQRFamidelike peptides in the rat central nervous system of rats. *J. Comp. Neurol.* 286: 269–287.

Laguzzi, R., Nosjean, A., Mazarguil, H. & Allard, M. (1996). Cardiovascular effects induced by the stimulation of neuropeptide FF receptors in the drosal vagal complex: an autoradiographic and pharmacological study in the rat. *Brain Res.* 711: 193–202.

Lenardo, M. J. & Baltimore, D. (1989). NF-kappa B: a pleiotropic mediator of inducible and tissue-specific gene control. *Cell* 58(2): 227–229.

Majane E. A. & Yang, H. Y. (1991). Mammalian FMRF-$NH_2$-like peptide in rat pituitary: decrease by osmotic stimulus. *Peptides* 12: 1303–1308.

Majane E. A., Zhu, J., Aarnisalo, A. A., Panula, P. & Yang, H. Y. (1993). Origin of neurohypophyseal neuropeptide-FF (FLFQPQRF-$NH_2$). *Endocrinology* 133: 1578–1584.

Okladnova, O., Syagailo, Y. V., Tranitz, M., Stöber, G., Rieder, P., Mössner, R. & Lesch, K.-P. (1998). A promoter-associated polymorphic repeat modulates PAX-6 expression in human brain. *Biochem. Biophys. Res. Commun.* 248: 402–405.

Sarge K. D., Murphy, S. P. & Morimoto, R. I. (1993). Activation of heat shock gene transcription by heat shock factor 1 involves oligomerization, acquisition of DNA-binding activity, and nuclear localization and can occur in the absence of stress. *Mol. Cell Biol.* 13(3): 1329–13407.

Verweij, C. L., Guidos, C. & Crabtree, G. R. (1990). Cell type specificity and activation requirements for NF-AT-1 transcriptional activity determined by a new method using transgenic mice to assay transcriptional activity if an individual nuclear factor. *J. Biol. Chem.* 265: 15788–15795.

Vilim, F. S., Aarnisalo, A. A., Nieminen, M.-L., Lintunen, M., Karlstedt, K., Kontinen, V. K., Kalso, E., States, B., Panula, P. & Ziff, E. (1999). Gene for pain modulatory neuropeptide NPFF: induction in spinal cord by noxious stimuli. *Mol. Pharmacol.* 55: 804–811.

Yang, H. Y. T., Fratta, W., Majane, E. A. & Costa, E. (1985). Isolation, sequencing, synthesis, and pharmacological characterization of two brain neuropeptides that modulate the action of morphine. *Proc. Natl. Acad. Sci. USA* 82: 7757–7761.

What is claimed is:

1. A promoter for a neuropeptide FF gene comprising a promoter-active DNA fragment located in the 5'-flanking region of the neuropeptide FF gene, wherein said promoter-active DNA comprises nucleic acid selected from the group consisting of SEQ ID NO:1, SEQ ID NO:3, SEQ ID NO:6; SEQ ID NO:7, SEQ ID NO:8, and SEQ ID NO:9.

2. The promoter of claim 1 wherein said promoter comprises transcription factor binding sites which modulate neuropeptide FF gene expression.

3. The promoter of claim 2 wherein said transcription factor binding sites affect autonomic nervous function, pain and hormonal dysfunction resulting from a central nervous system disorder.

4. A promoter for a neuropeptide FF gene comprising promoter-active DNA fragments located within nucleotide position 1 to position 2480 of SEQ ID NO:3.

5. The promoter of claim 4 wherein said promoter comprises transcription factor binding sites which modulate neuropeptide FF gene expression.

6. The promoter of claim 5 wherein said transcription factor binding sites affect autonomic nervous function, pain and hormonal dysfunction resulting from a central nervous system disorder.

7. A composition, comprising a coding region operationally coupled to a promoter and an acceptable carrier, wherein said promoter comprises promoter-active DNA fragments which are located in the 5'-flanking region of the human neuropeptide FF gene, wherein said promoter-active DNA comprises SEQ ID NO:3.

8. A composition of claim 7, wherein said promoter-active DNA fragments comprise DNA fragments located within nucleotide position 1–399 of SEQ ID NO:9.

9. A composition of claim 7, wherein said coding region is required in the treatment or diagnosis of a disease in a subject.

10. A composition of claim 8, wherein said coding region is required in the treatment or diagnosis of a disease in a subject.

11. A promoter for a neuropeptide FF gene comprising promoter-active DNA fragments located within nucleotide position 1 to position 9840 of SEQ ID NO:1.

12. A composition, comprising a coding region operationally coupled to a promoter and an acceptable carrier, wherein said promoter comprises promoter-active DNA fragments which are located in the 5'-flanking region of the mouse neuropeptide FF gene, wherein said promoter-active DNA is selected from the group consisting of bases 9516–9840 of SEQ ID NO:1, SEQ ID NO:6 and SEQ ID NO:7.

13. A composition of claim 12, wherein said promoter-active DNA fragments comprise DNA fragments located within nucleotide position 1 to position 9840 of SEQ ID NO:1.

14. A nucleic acid comprising nucleotides 9516–9840 of SEQ ID NO:1.

15. The nucleic acid of claim 14 comprising nucleotides 9262–9840 of SEQ ID NO:1.

16. The nucleic acid of claim 14 comprising nucleotides 9036–9840 of SEQ ID NO:1.

17. The nucleic acid of claim 14 comprising nucleotides 8756–9840 of SEQ ID NO:1.

18. The nucleic acid of claim 14 comprising nucleotides 8552–9840 of SEQ ID NO:1.

19. The nucleic acid of claim 14 comprising nucleotides 8314–9840 of SEQ ID NO:1.

20. The nucleic acid of claim 14 comprising nucleotides 7980–9840 of SEQ ID NO:1.

21. The nucleic acid of claim 14 comprising nucleotides 1–9840 of SEQ ID NO:1.

22. A nucleic acid comprising nucleotides 1–399 of SEQ ID NO:7.

23. A nucleic acid comprising nucleotides 1–398 of SEQ ID NO:8.

24. A nucleic acid comprising nucleotides 1–399 of SEQ ID NO:9.

25. A nucleic acid comprising SEQ ID NO:6.

26. A nucleic acid comprising SEQ ID NO:3.

* * * * *

SEQUENCE LISTING

<160> NUMBER OF SEQ ID NOS: 22

<210> SEQ ID NO 1
<211> LENGTH: 9840
<212> TYPE: DNA
<213> ORGANISM: Mouse

<400> SEQUENCE: 1

```
tctagacaga taccaggtac caatgttaaa tcatgatctt acgttttgtg tcagaactta      60
ttttgcatgc cattcatgac tctggagagt tttctccaaa aggaaagatg agattaattt     120
tcttttgcat tctttgtaat tatgacaaag aagagtcctt tctgttcctc tgtcctattt     180
tctaaccact tgctctctac tgtttgccct ccttcctggc agaaagtccc aaggaaagct     240
cagagccaac gggttctcca gccccagtga ttcagcacag ttccgcatca gccctagca      300
atggccttag tgttcgatct gcagctgaag ctgtggccac ctcggtcctc actcagatgg     360
ccagccaaag gacagaactg agcatgccca tacagtcaca tgtgatcatg accccacagt     420
cgcagtctgc gggcagatga tgcctcccat gatggagagg tccccagcca gagctcgccc     480
gcctgagcca agagagagat caacttaacc cctcctgtct gtcttggaat tgggcagaat     540
ggagagggag aaattgtgtg ttgtgagtat ggacagatgt ggggcttttc tctttagcca     600
catgatcatg tacgattaac acctgtacta ggcgcttctg gccccaaagc cacatagatc     660
atcccccaag ggtagggttt cttatgtacc tacagccaaa ggcctttcca tatggtctga     720
gcagtcatcc ctggccctga tgcatgtgtg cctgtctctt aacactaacc cttgcacttg     780
taggtttggg gtttctcagt gtcccctcct cccattgacc tgtggctgtt accttcttat     840
ttcttattag catgccactt cctgccagat ggagggaggt gagatttgat ggcgtgttac     900
ttgcttgtcc caccccctagc caccacatgc actcaggact ttgtctccca atagctgctt     960
atttgtctct ttcctccttc ctaaactgca gtgaaaacat tcacttgttg agaatgtaat    1020
acatttaatg tatgaggtag cagtgtttcc cacctcttcc atgtgcttta ttcctatctg    1080
ctaccaaaaa caaacacaaa caaaaaaagc aaaactctga gagtttgaat cattttttcat  1140
ttccaaatct attggtacct catttcgtct cttgactttc cttagtctag tggtggggtc    1200
tttcctactt ccccactagg ccttgggaac ctcatcttgt ggccttattg ttagtggcaa    1260
tgaaaaagga gagagctgga gacctaactg ggcttccctg tctccttccc taccctccag   1320
ttctaatcat cagggcagac aggaacagtg taatttaaaa cttgttccat caggttactg    1380
gattaactga ttcttttatg ttttacaaga gtttactggc caaagtctac atattgtcat    1440
ctttggtcat ctgtgctcct gcctctccac tgtgcttccc tgtccacatc actgcctgtt    1500
ccactataac tactttagct cagacctcct agagttgtca gacagtagct gcttccattc    1560
```

-continued

```
tctgtccctc ctacagctct cagcctccct tcttttctaa ggtatgtttt gtacccacca    1620
gtgtccagca ctctctcaac aaccttttca tcttctcacc cagttcttag cctacccact    1680
ggttgtctct agtcctgaaa tttcgttgaa cttgtccatg gtacaggctc cagggctctg    1740
aagcatcatg gttgaggtca tggatgcttt tgaatataag actgagtgga gagaggaggt    1800
atacattttc ctatgtataa tctcagcaga gcactcagga tatggcctgt ctgtgagatt    1860
gctgtctgtg gctgttggct gtccttattt tatgggttac agagagaaaa tacacccctc    1920
ctcttcttca tcttcccttg gctctgagct atgcaggctc ttccagagcc agaggcctgt    1980
ggatagatag gtcagcttta atagctcttg agttgagaat ccttcccatt gtcctagaac    2040
caccttctgc catctgctca agccaagtcc tcttttctag ctccatctta agtatgcaga    2100
ataattgctt gcgtctttgt cttccaaaat tcactgtcgt ggaggaatgg aaatgtcgtg    2160
tagcttatat gattatttcc tcagagttta gactagtgag cccatcctgt gacatgtttg    2220
tatgttttat gtaaatttcc ctcctgctct ttagagtcaa tgctgaacag gccacaccca    2280
gtgaaaacta ggaactggtt ttatagtctt ctcccacagg gtcttaacaa aaacatcccc    2340
tgaggtgaca aggatagcaa atgccacagc agatggttga gggcaagcca ccatctccag    2400
gggtttcact tggccttaga aactcacagc catagtttga gctcaggact tctttagatg    2460
gctgcttcct aggatttttt tttcctgctt atgaattttg tttcttttt tttaattgtc     2520
ttgatttccc agtagcagcc ttacactaaa atatgactga gcttatagct tccaagggcc    2580
cccccttggct atttctttcc tccatcagtc aagtgtttaa ttcagtgtaa cctaccagtc   2640
tgtcctggtt gcatgtctag tatacgtgga ggttcttttt cactttcttg acccttcatg    2700
tctgcttctc ttgagtcttt gtttttatag caggaagtta gtattggggg cttgaatgat    2760
gcagggcacc aacagaacca ttgcaggact gaaatcccca gactaccgat accttggtgg    2820
tcggttctca gcttcactaa gaaagcagaa cggctgctta tgctgaagcc tctgtgacag    2880
tcaagggggt catcacctac attattgctg ccaggggtca cagccctgac ctttgccttc    2940
cagacttaac tgaaccagaa ccagatacca tagaggatag caataaaccc ttcttgacat    3000
ctgactatga tgtgtcatag cggggtctct ggtcatgtct atttggggtt caatatgcct    3060
cttgtatttg aatgtcaact cctgtcccta ggtataggaa attttgtgat ataatttcat    3120
taaatagttt gactaattcc tttttaattt atctcaggtc ctccttctcc ccagtggctt    3180
ctgaggtttg tttggtcttt taagtatatt ccaagcttct tgaaaatact ggtaatatct    3240
atctctctct ttctctctct ctctctctgt ctctgtgtgt gtgtgtgtct gtctgtctgt    3300
ctgtctgtct gtctgtgtgt gtctgagtat atgattgttc caacttttgtg ctccactgca   3360
gaactgcatg atcttaatct cttggggaca cttttctagtg agggttttca ctttcatgtt   3420
tctttcatgt taatttctat cttgttcctt ttccatgttt gaatgccctc atcaaaatct    3480
ccctccatat atctgacttt ctcctccaac ttacccactg ttttgttcat tttggaggtt    3540
ttgtatacag ttcctagttc atgcatttgt atctgagact tctacatcaa ctctgaactc    3600
tttctcagac ttcagtac ttttggtttt cattaaggag aggtttgtag tatgccctgg       3660
tctgctgttg tctcatgttc cttgtgtttc tctgtggaat tttgtacatc agtcaggatg    3720
gctatgtcct ccagttttaa ctcatctttt cccaactctg ttttgtttca tgtaactaag    3780
cccttcttca gaggtctgtc agaaaggcgc tgagagtgtg atgtctcagg ccaggtgtg     3840
gtcagaggcc tggtctgtgc tcttgccacc cactccatat aacacagagt gttcagagtc    3900
tcaaaggtga gaagccgccc aacacgcagg gagagctggg aaggacacgg gccccttcat    3960
```

```
tcactttcac tcccttcctg ttggctgaga tgccagatct gcctgcttcc ttcctccact    4020
ccttcccatg gctgtaagca ccagaccaca tacttaaggg agctgtgctg gtgaaccttg    4080
ccttgctgcc tgccttccct ctcccattct gtagctcttg actccttcct tgattcacct    4140
cttccgtctc ctcagggacc cgccctccag caccatcatc ctgagagata taactgtact    4200
ttgtacagcc tgaaccgcca aaaagacaca catgcaattc ttcctctggc ttctgagagg    4260
ctccttaaag gtgctaactg ctcagctcac tctccccggc gtgtcccat  cctcagaaca    4320 catttccatt atctattgta cccaccaaaa agaaatatgt acttcttatg aaagaaaac    4380 cctagtctgt tcagatgtgt ctcacagctg tgtgacacgt gccttcgttg ctatgctttc    4440
tcctttcttt agccatgttt gaccagggtg ggagggtgga tcctaaagcc tatcaaaaga    4500
ccctacccca ctccagtcca gctagacatt cttcttacaa attctgtttc tgtctgtata    4560
tgtgcatatg catagacaaa tcccctatt  ccaccagcct ggtgatccat aggaatgagc    4620
agtgcctgct ggccacattc ccaccgtttg cactgttact ttgaggtaaa atcctaccct    4680
agaatgaaca aaggctggtg aaagtagggc agattaaggc agcttatgtt cttgtaaatg    4740
caagtttcta tttcagctag taggtgtttt ctttttctgt tttgttttt  aatgtagagc    4800 tggtaggcta taagccagca attgtgagta aggctttagc tattagtggc tgtgagcact    4860
agtttcattg actttacctt agggcagtgg ttctcagaac atggtccaag aacaacatca    4920
gcagcaccat cacctgaaga gcttgctaga aatgtacact ctgggccatc caacctcct     4980 gagttggcca ctctgaaggt gagctttaac taacagtctc tgctgctagt tcacactaat    5040
gcatgacagt ccctagcgga caggctggga gcatcttagc tctgggatga caacgattac    5100
tttaaatgtc ttctctgcct tagaattgat attttatt   cccccagtcc ttccttcctc    5160
ttccattaaa acagccacca ccacattact catctcaaat tctaggttgg tcttccttct    5220
agtcttagct ctaaaactct tgcctgcatt ggtctggact catatttcct tgcaggctac    5280
tagttctgca ttcttggtga ctttagccag caggaaggcc aggagtggtg gtggcatatg    5340
cctttgatcc cagcactttt gagggaagca gaggcaggca gatctctttg tgttcaagac    5400
cagtctggtc tacataggga gttcaaagcc aatcatagct atgcagtgag accctgtctc    5460
aaaacaaaca aacaaaatca gcaggagcct tagttgtcca tttcttccct gtgcacacac    5520
cacatctctt acaggaagat tagcctccac ccccacagtg gagcctccta catcctgata    5580
gagtatatgt tgagaagcca tgtgtatcta tgaatatagc tctgttctat atcctttga    5640 catgtagcaa tacctctcca tcctcaagga actcaaccca gtctgggtct ccccaggctc    5700
cagtggtaga ctctgacagg tgggaggata cagtgctctg ggctgttttg ttacaaaagt    5760
gtcttctgtc ctttccctcc tcccaattca gcatgacccc tgtgagcagg ctctcacaat    5820 ctcctgggc  agggctgagg caggggcttt cagctcttct ccataactat ccttcttcc     5880 ttcccccatg ccatttagca gttatcaccc agccttgcct ctccctcca  tcccttgccc    5940 tgacatatac tgtgccttat ttatgctgca aatataacat taaactatca agagaatgac    6000
tggtatgttt ggtgcttccc tacgcagact catgggccc  attggtcact cctagagact    6060
cagtaggcat ttgtgtctga ccatcctcct ccttccactt cttagggcag aactagcagg    6120
ctctctctgc tttcagtaag taacatggtg ttggaaaagg cacagagttc agatctttaa    6180
actgcctcag agccaaggca tcacaaaaag actgaccaat gggaatactg aacaccctgg    6240
ctctttcagt gttttatgct cacccacttc caacaattga aaggaagaaa aagtcctact    6300
```

```
cccaagaaag gggcttggga gtgtacaaag aggtagacaa agtcaagctt tctccagaga   6360
ctagaaggaa tagctgaaga gatggctcag tagttaagag gaaaaactgc tcttgtctca   6420
aaagatccgt ttggtcccca cacccatgtt ggctagttta ccaccaccct taactccagc   6480
tgcaagggat ctggtgccct cttttggccc ccacaggcac tgcactcact tgcataaccc   6540
ttcccccagc acacatatac acaattaaaa agttaaaaaa aaaaaaatta aaagagaag    6600
aagattggaa actcgaggca aactttgtaa aagcagatta aagctcacag gagaacaggt   6660
aatgatcagg gtgaggaagc ggacaggtga gccactgatc ctttctgtgt ctgtgtcttc   6720
cactaaaagt ggaaaccacc aaggagacag actgaagaac ctgacaaaag acagaacagg   6780
tacctctaag gttccttggt agaacagatc tactgggttg gtgtctggtg aaggactcag   6840
agcctcctta ggaaatggaa acacttactg gccatcactg tgtgggcccc agcaattaag   6900
gtacttactg ccaagcctga agacctgagc ttgatccctg gatacatgtg gtgggaagag   6960
aactggcaag gtgttctctg agctccacat atgctctgtg gggcatgtgt ctccttctcc   7020
ccaggtaaat aaatgaatga gaaagtgggt ggggagcaca cagtatgtcc aagaaagaga   7080
gaacattacc aaaagctaag acagagtctg gaggaagact ggagaggtgg ctcagtggtt   7140
aagagcactt gtgttctaga ggacttgagt tccgttccat ttaggtggct cacatctgga   7200
attctggact ttcggaagaa cagtcaggtg ctcttaccca ctgagccatc tcaccagccc   7260
caatattttt tttttttttt tttgagacag ggtttctctg tgtagctctc actgtcctgg   7320
aactcattct gtagaccagg ctggccttga actcagagat ttgccctacc tccaagtgc   7380
tgggactaaa ggcatatgtc accacaggcc agctgagatc ctgtatttaa ataaataagt   7440
ctggaaggtg ataaataaaa ctaagtctag aagatgagaa tcctagcaca caggttagga   7500
tgattaattt ttgttgaggt tagaagtgaa ccagcttctt tgtgaactta gtagcttcag   7560
cccagactcc ggtactgaag cagcagtgca gtgaacacag ggtggctgct gtgagactgc   7620
tgtgtacgca acccatctgc tgttcaggac agcttcctgt tcacagggtt aggttttttt   7680
attgttctct gggtgctgga gattgtgctc aggggcctcc agcaagttgc ctctttgttg   7740
ttttttttgtt tgtttgtttt gttttgaggc agggtttctc tgtgtagcct tggctgtttt   7800
ggaactagct ctgtagaaga gcctggcctc gactcaaaaa gatcagcctg cctctgaagt   7860
cacacagtga atttcgagag caaagataaa atacgaaatt tctgccaggt gtggtggtgc   7920
acatctgtaa tcccagcact tgagaaacta aaaacagagg ccagcatatt gggctacata   7980
cagagtctca ggcttagaaa accagacaag ctgggcactg tgacacacac tttaatccca   8040
gcacttggga ggcagaggca tcctaatcta catagtaaat tctagaccag ccaaggctaa   8100
atggtgacac ctgtttacac acacacacac acacacacac acacacacac acacacacac   8160
acacacacac acacagtgga gacaggaaaa gagagaggtg gggagagaaa ccgagaagac   8220
ccacaacaaa agcagcagtg aaatatttca actataatgt atgacaagct ctacaggaaa   8280
tcttgagaca aaccttacag aaaggttcac ccaagcctgg atgcattgta ttctagaaca   8340
tcagaaacct gatctagaag gtctccctct gcagtagagc acctgcctac catacacaag   8400
gctcttcatt tggacttgat tcccaagaaa gaaattttaa aatgccactt atccgcaaac   8460
ctaaaatgta agttggttcc aataaagtac ttccctgttg agcaaagaag atgtggatac   8520
atggtatttc tccaaaatatg tgagggggctt ttacatatga ctgagagata acctgagact   8580
ccattgaaca agctaggacc tctggtagag gccaccaaga agctaaagcc cactcagcac   8640
tctctggaga tggtaagttc cccaggactg gagtgggagg acagcaaagg gaatcacagt   8700
```

-continued

```
tgacattttg aaaacaccgg gtctgtgctt tcctacaaaa tgcatcccaa atgtttctcc      8760
tagcaagtaa ttcattttac tgttcccata tgtaagtgag gaaaaaaaga gtgtgagcag      8820
cttgctttgc tcatggggta gaaccccgac agtccttctt ctgtttaggc tagagacatg      8880
gtactctgac acctggattt gcaagtgagg ttaggactag ctcctttaaa ggacccttcc      8940
ctgaactgga gtgattgtct gtccctaaag cagaacccta gtcgccagct ccagtagtat      9000
attagaacca gaaccaggca gagcccatgc tgaccagacg gaactggaaa aatgtcacaa      9060
ttctgggccc caaagaacta ggtcctcaag tcctagacaa aatgtatgga aagggaaatg      9120
gctggacgtg gcagtgaaga gtagtggcca caaggtggca gcagagtttc agctgtggag      9180
gcccaatccc cagttctctt gcaaagatgg gcctgtccac aaaatttaca ggccacctct      9240
actcagtaag gctccaaaaa gagtctccta tctctcactt aactattcac aggtaaatct      9300
taaagggtag tgaacccaca tttaacctga ctagaagcag tggggattga aatgggctg       9360 tggtcctgat cacccattcc aggcaggagt agggaccaag ctggttcacc ctagcctgca      9420
cttaacacta gttccttccc atccaggaca taatgcccaa ttctgacagg agtttctcca      9480
gtcaggaaca agaggtgatc aattgaagct tctccaatct gttgaaggat tggaggttct      9540
tctaaggttc ccccagggtc taactctgac aaactgtctg caattaatga tgcttcctga      9600
gctccggaga caagatttat gcatctaata aagtctatat aactccaggc ttaggctggg      9660
ggggaggaag ctaagagcag agagtcccca ggggagtacg ggagggggg tcccaggtgg       9720 ctcttaatag agccatgcat ttccattgct tgtctagatt tccccccagg ctgccggtga      9780
ggtgggggta gggacatcag gtataagaag accgtgggca ctcaggaggc agatggcagc      9840
```

<210> SEQ ID NO 2
<211> LENGTH: 5124
<212> TYPE: DNA
<213> ORGANISM: Mouse

<400> SEQUENCE: 2

```
atggactcca agtgggctgc tctgctgctg ctgctactgc tgctgctgaa ttggggccac        60
actgaagagg cagggagctg gggtgaagac caagtctttg cagtgagtga acatcctgct       120
gccccatcca cccagccgcc atctctcctt cagctgaaac ttatgataca gggtttggtg       180
ttccccaggc tgctaaggtc ttcaaaaagt ctggcttcta agggagggaa atggcttctc       240
agcccacgca agtttcccct agaagccatt ctttccctcc atgtcttcag tgtacaagac       300
actgccaggt tccttccctg ccactctctc atcacaggga gaagataagg acccccaccc       360
accacagtat gcccacattc cagacaggat ccagactcct gggtccctct ttcgtgttct       420
gctccaggcc atggacacac ctagaaggag cccagccttc ctgtttcagc cccagaggtg       480
agttccaaag ggaagaggct gagaagggtg gagggcagag gaagatgtga gagaaggtga      540
gatggaggga gtgccaacta aggatgaatc tctcctaagg tttggcagaa gtgcatgggg       600
gtcctggagc aaggaacagc taaatccgca ggccagacag ttctggagcc tggccgctcc       660
tcagcgcttt gggaagaagt agcatcgtca gctgtgatgc ctgcatgcaa aaccacttcc       720
ccatgttccc tgtgtgcccc caaataaaaa tggtccggct ggcttcagaa tccctgtgtt       780
tggacaagac tgtcagggag caggtgggag cccaagggca atagctgtag ccccccttca      840
cctccactca gtctctagcc attctgttgt taaggatccc caaggctact actgcaccttt      900 gcctcctctc ggtaacaaaa aagaacaagg ggttcaaaag gagaacaagc tcaccatgtt       960
```

-continued

```
tattccttat accctcatga cccaaggcca gagagagcag ggttttggaa gccaaagagc    1020
agcatttatt caggactcca atagattcat ccatcaccca cggaatgagg acaaatcctg    1080
tgctggctgg ggccctgtgg ttcatggctc cttgcttgcc tgtgccttcc tcagtctcaa    1140
ggcagacagg ctgtgtcaga ggtagagatg gcacttctgg agggtaccag agctaggtgg    1200
atacatggac ccaggggcag aaggagcaag aagtaaaaga tgcatatcca tcactgcagt    1260
gggatgctac ttgctacccg ccatgatcct gaggtactgt agggcgcggt gagcagcatc    1320
acctcgggct gcctccctgg tggttgcaga accataacac acagtggctg gctgggtgga    1380
cagttccact aggcactggc agagcccact caggctcagt tcctctggaa accaagaaag    1440
agaagggagg cactggtggg gaaggggcac caaacagtgt acacatcacc catctcccaa    1500
ctccttcata cttgctttga tccagtcccc tccatcccca gtctctagtt ggccatacca    1560
atatccagat agctgacatg gaaagcctgc tcctcagaga gctcactgag gacactgcag    1620
caggcagagc ccagagcccc tagagagccc acggagcaac tgcgaaggga taggatcttt    1680
tctcccacag aattccgcaa ggaatcccag gtgcagcctg ccccacgatt cctcagtcca    1740
tccaggcggg agctcacgcc ctaatgagat aagagtgaga aagcagctaa ggactgtggg    1800
acccaagaac tgggtattat gctctgactc ctggcagcct tcctcatccc aggaaaagtt    1860
gcctataggg gctttgccct aggccagctt tcactagtga ccctacatat aggctgaggg    1920
gacttctggg cgcacaggtt caaggagccc tgggaaggaa agcaggccca tactcacttc    1980
caaaccacag acccaaccca attccgtacc atgtcctgca gtgtgaacca catgtcgagc    2040
ccacacaagc cacttacaat ggaaaaatga tcgtcatcag gctctgcctc attgccatcc    2100
cgggcatcca gaggtacaag tgtgcactcg aaggagcatc ttagctgctg cgttacgctt    2160
tgccagcttt ttggaagtgc cactgcctga gggtggggga aggaattgtt caacttgggg    2220
attcctaaca gaccaatgct ttcctctagg gtaacttaga cagtcaccca atgagatacc    2280
actgcaaaga ggagctcaag gcctgatctt tttaactgag gagttggtga gccagataag    2340 aggggggaaag atgggcaggg acaagggaga gacaggaagg caggagctga gcaaggacct    2400
gcaaagcaaa ggaagctggg acagagcaca gccaggcaaa gaaccacctt gtgtttgggg    2460
ttacagtgtg gcaaagagag aaggtgagtg aaccccccttt tccccagtta ccaatctcaa    2520
tgaaacgctc caccggcaa gtcatggtga actctttgcg gtgagcaggc ccagactctt    2580
gggtcaccat gtactctggc aaacgccagc ctttttgcac caccagctcc ttgaaagaaa    2640
accataagag agtccaaggc ttagtgagga aagggtcctt agccaatggc cttctaccaa    2700
gagcctccac ctttgagtga aaggaggac caccctaccc acaagtgcac acgcccctgc    2760
ctcagcccta cttcagagaa gatagcacac atgacaatga agacgaggca cacctgcaga    2820
gcaccgacgg ggttgcactc agactgctga ggagagacag ggggctgcat ctccatggga    2880
gggctcctaa agaaaaaagg gcccaggcca gtgctgagga aaatgcagag gttcctcctg    2940
tcctggtcat ggatcaagtg ccagccacta ccacctccca attcctcacc aggcaggcag    3000
ctatctgtcc aaacatctag cctttctcct ccctccccac accccaccaa gtgaggctct    3060
gctacttccc aggagcactt agatgtggaa atccttcagc aatgtccctg tgatggaggt    3120
aaaggagctg tacacacagt cctggaagta cctttttgggt ctcaaacatg gagcctctaa    3180
gatgtttaaa caatctaaca ttcattgctt ggctatttaa tcatcataaa ttacctccta    3240
gctcaggctt accaaccagc tggtgcaaat ttttcaatta caccagtctg tctttactct    3300
caggcttcct catcctgacc tgcctgagtc caagagctat gagactagaa gccaagaccc    3360
```

```
cctccttcct ccaagacgtc aggggactca agatacctgg ttagtacagc agatggaaca    3420
ggggcagcag cttctgcagc aacgacagga gtgtcctcag gcggtgaaga gtctaggaga    3480
gaaaaagaac ttcccgaggg gaagaaggtc ttggattcac acccatgtag aagggaatga    3540
gggtgtgagg tccttctgac ctttccatcc cctgagaact ccttcccccc gatgcagact    3600
cggagagcct cagcaacagc tcttcctcct gggatcctct gctgacccca cactggctca    3660
gaagcactga ggttagggtg ggggctcaga aaagagtctc tttctaccca acaagctgca    3720
acctgaatgt ggaagaggga aagccatctt gctagaaaga gggggcatgc caggaccaac    3780
tttatcagtc tttgcctcca ccccctatgc cttttctca tgcccagag cagccaccac    3840 ccatcaaagg gggctggcta ttactctgag gcactctaga aacaccctgt tcagcttcag    3900
aggaaattct caggaagggg ccacgagagg gtggccatga gtcaccagac caggcttagg    3960
gagagaagta gatagtgcag aggcctgggt tctcagcggg cttctagtgt gccttggctg    4020
ttcctccctc acctgctgtc ctccagggct ggttccagca tgctcccccc tttgaggtgt    4080
ttgagggcca cctcagctgc cttgtgcttg gctgccttct tgctgggcc ctgacctaag    4140 aaaaggggcg tgggcaatac tggaggtcac cggcaggaca gcagagaaac cagcccccac    4200
agcctatctc ctcatagcca gagggagtga gaagagccct ctgaccaacc tccctgtca    4260 gaactggaag ggttctacta attgttggac tagcctttt cctagttagc attaacagtc    4320
aacttggcac aacctaggat ctaaaaggat ctgaaaggag agccttaact gaggaattgc    4380
ctacatcagc ctggcctgag ggcatgtctg ggggtgggtg gggggatgg actgatagtt    4440 aattgatgct gatatgcaca gcccactatt gtggtaccac ccctaggcag gtggtcctga    4500
actgtgtaag aaatctagta gagtataaat aagccagcca gccagcatgg agtatctgcc    4560
attgttcctg ctgtgcttct gtggctgtga agtgagttcc ttagtcagaa gtagcaagaa    4620
tcagattatt ttctttggtc ttgactgata atgtgagttt cttccttagc ttcccttagt    4680
catgaatgta acctgaactg taaacctatc aacccttttc ctcctctaaa ctgcttttag    4740
tttcggagcc ttactacagc aacagaaatg ggccttgaac acctcctctt tcagtcagct    4800
cccgtaatga aactgtgcca ggcaggattt ttgagctcca acactggtgg gttgcggagg    4860
gatgttttgc tctgtctttc tttcccctt tctcttccct cggtaaatag gaaatagaga    4920
caactgaggg tctgaagtca aagctctgct ctgccactta ttacatgtga actggagcct    4980
accatttaat ttctcatact aagttcttcg tgttcaatgt gaggcatgaa ggctagcaga    5040
gtatgtgctc cccctaatac ccacgaggag ttcaatgtct catttactct tcctctgggg    5100
tgataaagta gcagatccga attc                                            5124
```

<210> SEQ ID NO 3
<211> LENGTH: 2480
<212> TYPE: DNA
<213> ORGANISM: Homo sapiens

<400> SEQUENCE: 3

```
tggcttagtc cgcattaaca gaaatatggt atctggagca tccagatcca aacctgctct      60
aatctacgtg tctaaaggat aagttggttc ctagatgcct tgccttaaag agtggggtgc     120 ttcccttga gcaaaaaga ctatggagtg ggccaggtgc ggtggctcac gcctgtaatc     180
ccaacacttt gggatgccaa ggtgggtgga ttgcttgagg tcaggagttc aagaccagcc     240
tggccaacat ggtgaaaccc catctctact cccctacaa aaattagccg ggcatagtgg     300
```

-continued

```
tgtgtgcctg taatcccagc tacttgggag gctgaggcag gagaatcgcc tgaacccggg    360
aggcagaggg gttgcggtga gccgagatcg caccactgca ctccagcctg ggtgacagag    420
ccagactcca tcgtaaaaaa aaaaaaaaaa agctggagt gtaagaatga actctctctt    480
caaaaatatg aagagctttt acacatgaaa gagatgagat gttctgttga gacttaatgg    540
agcaaactaa gaccccgagt agaagtcaca ggaagcccaa agcccctcg gcacaaggat    600 aaatattgtc cgaagactgt ctgaggagat ggtaagttcc ccgactgggg cacatgaggc    660
aatcacagct aacgttttga ggatacctgt tctatgcaag ctgttttatt gaatggatta    720
caaaaagtat gttaagtaat gcacacccta ggaaggcgtt ccttgtaaaa tgggcccatg    780
tttcaggtga ggaaactgaa gctcagagcg ggagacagct tgctcaagca gaggccaagg    840
cctttacgtc atggctcttc ctcagcacaa gctagagacc cacactggtg gggatgctcc    900
aaaagggact cgaggattag aaggaacctg caccatatgg ctttgaaggc ctctcccta    960 ggattagtga ttctgatttt tcttaagaca ggattctagg ctactctata tgagagccag   1020
ggccaggcag aggctgtgga gaccagagtc ggggtcagaa tgatagtcca gccccacagt   1080
agcctgctcc tgtccttctg ggactccctg gagactggac cctagcacct ccactcagcc   1140
tcaccctcct cacttcctct gcagaggtct attctaggaa aaggaaatgg ccggagctgg   1200
caatgaggag ctgtgaccac agggtggcag cagtgcttca gctgtggaga gtgactatag   1260
gaagggcgat gaggcaggtc ggaagcagtg ctctctagtg aggatggggg tctgtctgca   1320
aagattggaa gccacactca ttcagtgggc tccaaaatcc tgtagcctcc ctctatatct   1380
taataatttt tttttttga gacagagttt ctcttttttgc caaggctgga gtgtagtggt   1440
gccatctcag ctcactgcaa cctctgcctc cccgattcaa gcgattctcc tgcctcagcc   1500
tcctgagtag ctgggattac aggtgcctac caccacgccc agctaatttt tgtattttta   1560
gtagacaggg gtttcaccat gttggccagg ctggtctcga actcctgccc tcaggtgatc   1620
cacccgcctt ggtctcccaa agtgctgggg ttacaggtgt gaggcactgc acccggcaaa   1680
aaaaaaatgg ttttttaatta aaaaaaaaaa gatacaggct gggcatggtg gttgacgcct   1740
gtagtcccag ctacttggga ggctgaggca ggagaatcac ttgaacccag gagccagagg   1800
ttgcagtgag ccgagatcgc gccactgcac tccagcctgg gcaaaagag cgaaactcca   1860 tctcaaaaag aaaaaaagtt aaattctctc catcatcatg aagttgaata tatttttttct   1920 atccacaggc aaatctgagt agcctccaag aggcacacaa gcagaggatg ggctgtgttg   1980
ccctgactgc cagccccagg cacagaggac caggcctggt catcctcaca gactctgacc   2040
ctggctcttc ccactcctct tccactccag gacatcctac ttaaccccctc ctgacatgag   2100 tttcttgtgc tttagtctac aggttaggaa agaggggaag tgataaacaa gctctccaac   2160
ctgttgaggg attaggggtt cgtctaaggc tccccagggc ctggctctga caaagcgtct   2220
gcaactaatg atgcttcttg agctctggag acaggattta tgcatctaat aaagtctgta   2280
actccaggct taggggccgg gggcaggagg ctgagagcat gaagtcctgg gggcgccatg   2340
ggaggagatc ccaggtggct cctaatgagc cctgcatttc atttgcctgc tctagattcc   2400
cctaaggcta ctgtgaggct gggggtgggg gaacagcagg tataagaggt tggggtggct   2460
gtaggagggt aggtggcagc                                               2480
```

<210> SEQ ID NO 4
<211> LENGTH: 396
<212> TYPE: DNA
<213> ORGANISM: Mouse

```
<220> FEATURE:
<221> NAME/KEY: CDS
<222> LOCATION: (7)..(393)

<400> SEQUENCE: 4 gtatct atg aat ata gct ctg ttc tat atc ctt ttg aca tgt agc aat        48
       Met Asn Ile Ala Leu Phe Tyr Ile Leu Leu Thr Cys Ser Asn
       1               5                   10 acc tct cca tcc tca agg aac tca acc cag tct ggg tct ccc cag gct        96
Thr Ser Pro Ser Ser Arg Asn Ser Thr Gln Ser Gly Ser Pro Gln Ala
15                  20                  25                  30 cca gtg gta gac tct gac agg tgg gag gat aca gtc ctc tgg gct gtt       144
Pro Val Val Asp Ser Asp Arg Trp Glu Asp Thr Val Leu Trp Ala Val
                35                  40                  45 ttg tta caa aag tgt ctt ctg tcc ttt ccc tcc tcc caa ttc agc atg       192
Leu Leu Gln Lys Cys Leu Leu Ser Phe Pro Ser Ser Gln Phe Ser Met
            50                  55                  60 acc cct gtg agc agg ctc tca caa tct cct ggg gca ggg ctg agg cag       240
Thr Pro Val Ser Arg Leu Ser Gln Ser Pro Gly Ala Gly Leu Arg Gln
65                  70                  75 ggg ctt tca gct ctt ctc cat aac tat ccc ttc ttc ctt ccc cca tgc       288
Gly Leu Ser Ala Leu Leu His Asn Tyr Pro Phe Phe Leu Pro Pro Cys
        80                  85                  90 cat tta gca gtt atc acc cag cct tgc ctt ctc cct cca tcc ctt gcc       336
His Leu Ala Val Ile Thr Gln Pro Cys Leu Leu Pro Pro Ser Leu Ala
95                  100                 105                 110 ctg aca tat act gtg cct tat tta tgc tgc aaa tat aac att aaa cta       384
Leu Thr Tyr Thr Val Pro Tyr Leu Cys Cys Lys Tyr Asn Ile Lys Leu
                115                 120                 125 tca aga gaa tga                                                       396
Ser Arg Glu <210> SEQ ID NO 5
<211> LENGTH: 129
<212> TYPE: PRT
<213> ORGANISM: Mouse

<400> SEQUENCE: 5

Met Asn Ile Ala Leu Phe Tyr Ile Leu Leu Thr Cys Ser Asn Thr Ser
1               5                   10                  15

Pro Ser Ser Arg Asn Ser Thr Gln Ser Gly Ser Pro Gln Ala Pro Val
                20                  25                  30

Val Asp Ser Asp Arg Trp Glu Asp Thr Val Leu Trp Ala Val Leu Leu
            35                  40                  45

Gln Lys Cys Leu Leu Ser Phe Pro Ser Ser Gln Phe Ser Met Thr Pro
        50                  55                  60

Val Ser Arg Leu Ser Gln Ser Pro Gly Ala Gly Leu Arg Gln Gly Leu
65                  70                  75                  80

Ser Ala Leu Leu His Asn Tyr Pro Phe Phe Leu Pro Pro Cys His Leu
                85                  90                  95

Ala Val Ile Thr Gln Pro Cys Leu Leu Pro Pro Ser Leu Ala Leu Thr
            100                 105                 110

Tyr Thr Val Pro Tyr Leu Cys Cys Lys Tyr Asn Ile Lys Leu Ser Arg
        115                 120                 125

Glu

<210> SEQ ID NO 6
<211> LENGTH: 1920
<212> TYPE: DNA
```

-continued

<213> ORGANISM: Mouse

<400> SEQUENCE: 6

| tacagagtct | caggcttaga | aaaccagaca | agctgggcac | tgtgacacac | actttaatcc | 60 |
| cagcacttgg | gaggcagagg | catcctaatc | tacatagtaa | attctagacc | agccaaggct | 120 |
| aaatggtgac | acctgtttac | acacacacac | acacacacac | acacacacac | acacacacac | 180 |
| acacacacac | acacacagtg | gagacaggaa | aagagagagg | tggggagaga | aaccgagaag | 240 |
| acccacaaca | aaagcagcag | tgaaatattt | caactataat | gtatgacaag | ctctacagga | 300 |
| aatcttgaga | caaaccttac | agaaaggttc | acccaagcct | ggatgcattg | tattctagaa | 360 |
| catcagaaac | ctgatctaga | aggtctccct | ctgcagtaga | gcacctgcct | accatacaca | 420 |
| aggctcttca | tttggacttg | attcccaaga | aagaaatttt | aaaatgccac | ttatccgcaa | 480 |
| acctaaaatg | taagttggtt | ccaataaagt | acttccctgt | tgagcaaaga | agatgtggat | 540 |
| acatggtatt | tctccaaata | tgtgagggc | ttttacatat | gactgagaga | taacctgaga | 600 |
| ctccattgaa | caagctagga | cctctggtag | aggccaccaa | gaagctaaag | cccactcagc | 660 |
| actctctgga | gatggtaagt | tccccaggac | tggagtggga | ggacagcaaa | gggaatcaca | 720 |
| gttgacattt | tgaaaacacc | gggtctgtgc | tttcctacaa | aatgcatccc | aaatgtttct | 780 |
| cctagcaagt | aattcatttt | actgttccca | tatgtaagtg | aggaaaaaaa | gagtgtgagc | 840 |
| agcttgcttt | gctcatgggg | tagaaccccg | acagtccttc | ttctgtttag | gctagagaca | 900 |
| tggtactctg | acacctggat | ttgcaagtga | ggttaggact | agctccttta | aaggaccctt | 960 |
| ccctgaactg | gagtgattgt | ctgtccctaa | agcagaaccc | tagtcgccag | ctccagtagt | 1020 |
| atattagaac | cagaaccagg | cagagcccat | gctgaccaga | cggaactgga | aaaatgtcac | 1080 |
| aattctgggc | cccaaagaac | taggtcctca | agtcctagac | aaaatgtatg | gaaagggaaa | 1140 |
| tggctggacg | tggcagtgaa | gagtagtggc | cacaaggtgg | cagcagagtt | tcagctgtgg | 1200 |
| aggcccaatc | cccagttctc | ttgcaaagat | gggcctgtcc | acaaaattta | caggccacct | 1260 |
| ctactcagta | aggctccaaa | aagagtctcc | tatctctcac | ttaactattc | acaggtaaat | 1320 |
| cttaaagggt | agtgaaccca | catttaacct | gactagaagc | agtggggatt | gaaatggggc | 1380 |
| tgtggtcctg | atcacccatt | ccaggcagga | gtagggacca | agctggttca | ccctagcctg | 1440 |
| cacttaacac | tagttccttc | ccatccagga | cataatgccc | aattctgaca | ggagtttctc | 1500 |
| cagtcaggaa | caagaggtga | tcaattgaag | cttctccaat | ctgttgaagg | attggaggtt | 1560 |
| cttctaaggt | tcccccaggg | tctaactctg | acaaactgtc | tgcaattaat | gatgcttcct | 1620 |
| gagctccgga | gacaagattt | atgcatctaa | taaagtctat | ataactccag | gcttaggctg | 1680 |
| ggggggagga | agctaagagc | agagagtccc | caggggagta | cgggaggggg | ggtcccaggt | 1740 |
| ggctcttaat | agagccatgc | atttccattg | cttgtctaga | tttccccca | ggctgccggt | 1800 |
| gaggtggggg | tagggacatc | aggtataaga | agaccgtggg | cactcaggag | gcagatggca | 1860 |
| gcatggactc | caagtgggct | gctctgctgc | tgctgctact | gctgctgctg | aattggggcc | 1920 |

<210> SEQ ID NO 7
<211> LENGTH: 411
<212> TYPE: DNA
<213> ORGANISM: Mouse

<400> SEQUENCE: 7

| tccaggacat | aatgcccaat | tctgacagga | gtttctccag | tcaggaacaa | gaggtgatca | 60 |
| attgaagctt | ctccaatctg | ttgaaggatt | ggaggttctt | ctaaggttcc | cccagggtct | 120 |

```
aactctgaca aactgtctgc aattaatgat gcttcctgag ctccggagac aagatttatg    180
catctaataa agtctatata actccaggct taggctgggg gggaggaagc taagagcaga    240
gagtccccag gggagtacgg gagggggggt cccagtggc tcttaataga gccatgcatt    300
tccattgctt gtctagattt cccccaggc tgccggtgag gtgggggtag ggacatcagg    360
tataagaaga ccgtgggcac tcaggaggca gatggcagca tggactccaa g           411

<210> SEQ ID NO 8
<211> LENGTH: 410
<212> TYPE: DNA
<213> ORGANISM: Rat

<400> SEQUENCE: 8
tccaggacta taatgctcaa tcctgacagg agtttcttca gtcaggaaca agaggtgatc     60
aattgaagct tctccaacct gttgaaggat tggaggttct tgtaagactc ctccagggcc    120
tagctctgac aaactgtctg caattaataa tgcttcctga gctctggaga caagatttat    180
gcatctaata aagtctataa ctccaggctc atgctgggg tagagaactg agagcagaaa    240
gtctcccagg gcggtatggg aggggggtcc caggtggctc ttaatagagc catgcatttc    300
cattgcctgt ctagatttcc cccaggctgc tgatgaggtg ggggtagggg acatcaggta    360
taagaagccc gtgtgccacg gaggaggcag atggcagcat ggattccaag              410

<210> SEQ ID NO 9
<211> LENGTH: 411
<212> TYPE: DNA
<213> ORGANISM: Homo sapiens

<400> SEQUENCE: 9 taaccctcc tgacatgagt ttcttgtgct ttagtctaca ggttaggaaa gaggggaagt     60
gataaacaag ctctccaacc tgttgaggga ttaggggttc gtctaaggct ccccagggcc    120
tggctctgac aaagcgtctg caactaatga tgcttcttga gctctggaga caggattttat   180 gcatctaata agtctgtaa ctccaggctt aggggccggg ggcaggaggc tgagagcatg    240
aagtcctggg ggcgccatgg gaggagatcc caggtggctc ctaatgagcc ctgcatttca    300
tttgcctgct ctagattccc ctaaggctac tgtgaggctg ggggtggggg aacagcaggt    360
ataagaggtt ggggtggctg taggagggta ggtggcagca tggattctag g            411

<210> SEQ ID NO 10
<211> LENGTH: 417
<212> TYPE: DNA
<213> ORGANISM: Artificial Sequence
<220> FEATURE:
<223> OTHER INFORMATION: Description of Artificial Sequence: Consensus
      sequence for NpFF promotor region
<220> FEATURE:
<221> NAME/KEY: unsure
<222> LOCATION: (9)
<223> OTHER INFORMATION: n = unknown
<220> FEATURE:
<221> NAME/KEY: unsure
<222> LOCATION: (17)
<223> OTHER INFORMATION: n = unknown
<220> FEATURE:
<221> NAME/KEY: unsure
<222> LOCATION: (38)
<223> OTHER INFORMATION: n = unknown
<220> FEATURE:
<221> NAME/KEY: unsure
<222> LOCATION: (41)
<223> OTHER INFORMATION: n = unknown
```

<220> FEATURE:
<221> NAME/KEY: unsure
<222> LOCATION: (113)
<223> OTHER INFORMATION: n = unknown
<220> FEATURE:
<221> NAME/KEY: unsure
<222> LOCATION: (197)..(198)
<223> OTHER INFORMATION: n = unknown
<220> FEATURE:
<221> NAME/KEY: unsure
<222> LOCATION: (215)
<223> OTHER INFORMATION: n = unknown
<220> FEATURE:
<221> NAME/KEY: unsure
<222> LOCATION: (220)
<223> OTHER INFORMATION: n = unknown
<220> FEATURE:
<221> NAME/KEY: unsure
<222> LOCATION: (226)
<223> OTHER INFORMATION: n = unknown
<220> FEATURE:
<221> NAME/KEY: unsure
<222> LOCATION: (249)
<223> OTHER INFORMATION: n = unknown
<220> FEATURE:
<221> NAME/KEY: unsure
<222> LOCATION: (252)
<223> OTHER INFORMATION: n = unknown
<220> FEATURE:
<221> NAME/KEY: unsure
<222> LOCATION: (257)
<223> OTHER INFORMATION: n = unkown
<220> FEATURE:
<221> NAME/KEY: unsure
<222> LOCATION: (260)
<223> OTHER INFORMATION: n = unknown
<220> FEATURE:
<221> NAME/KEY: unsure
<222> LOCATION: (262)
<223> OTHER INFORMATION: n = unknown
<220> FEATURE:
<221> NAME/KEY: unsure
<222> LOCATION: (339)
<223> OTHER INFORMATION: n = unknown
<220> FEATURE:
<221> NAME/KEY: unsure
<222> LOCATION: (357)
<223> OTHER INFORMATION: n = unknown
<220> FEATURE:
<221> NAME/KEY: unsure
<222> LOCATION: (375)
<223> OTHER INFORMATION: n = unknown
<220> FEATURE:
<221> NAME/KEY: unsure
<222> LOCATION: (388)
<223> OTHER INFORMATION: n = unknown

<400> SEQUENCE: 10
tccaggacna taatgcncaa ttctgacagg agtttctnca ngtcaggaac aagaggtgat      60
caattgaagc ttctccaacc tgttgaagga ttggaggttc ttctaaggct ccnccagggc     120
ctagctctga caaactgtct gcaattaatg atgcttcctg agctctggag acaagattta     180
tgcatctaat aaagtcnnta taactccagg cttanggctn ggggnagga agctgagagc     240 agaaagtcnc cngggnggn cnggggnggg ggtcccaggt ggctcttaat agagccatgc     300
atttccattg cctgtctaga tttcccccca ggctgctgnt gaggtggggg tagggnaca     360 tcaggtataa gaagnccgtg tggcactnag gaggcagatg gcagcatgga ttccaag      417

<210> SEQ ID NO 11
<211> LENGTH: 18
<212> TYPE: DNA
<213> ORGANISM: Artificial Sequence
<220> FEATURE:

```
<223> OTHER INFORMATION: Description of Artificial Sequence: antisense
      primer for mouse

<400> SEQUENCE: 11
tggagtccat gctgccat                                                    18

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:sense primer
      for 325 bp mouse promoter

<400> SEQUENCE: 12
gtgctagcaa tctgttgaag gattgg                                           26

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:sense primer
      for 579bp  mouse promoter

<400> SEQUENCE: 13
gtgctagcag tctcctatct ctcact                                           26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:sense primer
      for 805bp mouse promoter

<400> SEQUENCE: 14
gtgctagcag acggaactgg aaaaat                                           26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:sense primer
      for 1085bp  mouse promoter

<400> SEQUENCE: 15
gtgctagctc tcctagcaag taattc                                           26

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence:sense primer
      for 1289bp mouse promoter

<400> SEQUENCE: 16
gtgctagcta catatgactg agagat                                           26

<210> SEQ ID NO 17
<211> LENGTH: 26
<212> TYPE: DNA
<213> ORGANISM: Artificial Sequence
<220> FEATURE:
```

```
<223> OTHER INFORMATION: Description of Artificial Sequence:sense primer
      for1527bp mouse promoter

<400> SEQUENCE: 17
gtgctagcag cctggatgca ttgtat                                              26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence:sense primer
      for 1861bp mouse promoter

<400> SEQUENCE: 18
gtgctagcac agagtctcag gcttag                                              26

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: antisense
      primer for human

<400> SEQUENCE: 19
gctgccacca cctaccctcc tac                                                 23

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: antisense
      primer for rat

<400> SEQUENCE: 20
caccccagct ccctgcctct t                                                   21

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: antisense
      primer for nested human

<400> SEQUENCE: 21
gtggatccat ctagagcagg caaatg                                              26

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: antisense
      primer for nested rat

<400> SEQUENCE: 22
cgtggcccca gttcctcagc a                                                   21
```